US010537718B2

(12) United States Patent
Lederman et al.

(10) Patent No.: US 10,537,718 B2
(45) Date of Patent: Jan. 21, 2020

(54) VASCULAR DILATORS

(71) Applicants: The United States of America, as represented by the Secretary, Department of Health and Human Services, Bethesda, MD (US); Henry Ford Health System, Detroit, MI (US)

(72) Inventors: Robert Jay Lederman, Chevy Chase, MD (US); Ozgur Kocaturk, Rockville, MD (US); Adam Brett Greenbaum, Detroit, MI (US)

(73) Assignees: THE UNITED STATES OF AMERICA, as represented by the Secretary, Department of Health and Human Services, Bethesda, MD (US); Henry Ford Health System, Detroit, MI (US)

( * ) Notice: Subject to any disclaimer, the term of this patent is extended or adjusted under 35 U.S.C. 154(b) by 475 days.

(21) Appl. No.: 15/025,336

(22) PCT Filed: Oct. 13, 2014

(86) PCT No.: PCT/US2014/060270
§ 371 (c)(1),
(2) Date: Mar. 28, 2016

(87) PCT Pub. No.: WO2015/057573
PCT Pub. Date: Apr. 23, 2015

(65) Prior Publication Data
US 2016/0235952 A1 Aug. 18, 2016

Related U.S. Application Data

(60) Provisional application No. 61/890,961, filed on Oct. 15, 2013.

(51) Int. Cl.
A61M 29/00 (2006.01)
A61B 17/34 (2006.01)
(Continued)

(52) U.S. Cl.
CPC ....... A61M 29/00 (2013.01); A61B 17/00234 (2013.01); A61B 17/3478 (2013.01);
(Continued)

(58) Field of Classification Search
CPC .. A61M 29/00; A61M 25/0662; A61M 29/02; A61M 2029/025;
(Continued)

(56) References Cited

U.S. PATENT DOCUMENTS 5,312,341 A * 5/1994 Turi ...................... A61M 25/10
128/898
5,312,360 A  5/1994 Behl
(Continued)

FOREIGN PATENT DOCUMENTS

EP 0334116 9/1989
EP 1382309 1/2004
EP 2279702 2/2011

OTHER PUBLICATIONS

Supplementary European Search Report for related European Application No. EP 14 85 4262, 8 pages, dated Apr. 20, 2017.
(Continued)

Primary Examiner — Bhisma Mehta
Assistant Examiner — Hamza A Darb
(74) Attorney, Agent, or Firm — Klarquist Sparkman, LLP

(57) ABSTRACT

Technology disclosed herein provides a reduced transition between the edge of a rigid vascular dilator and the distal edge of the accompanying introducer sheath. Disclosed dilators can be segmented into two or more primarily
(Continued)

longitudinally extending parts, can have rigid circumferential or semi-circumferential leading shoulders to minimize the transition between the dilator and the sheath edge, and can contain internal recesses to allow sequential retraction of segments once the introducer sheath is delivered to a target chamber. With this technology, vascular introducer sheaths can be introduced percutaneously into a broad range of diseased target vessels and chambers with reduced damage to the wall of the vessel or chamber, and with reduced damage to the distal end of the introducer sheath.

26 Claims, 18 Drawing Sheets

(51) Int. Cl.
*A61B 17/00* (2006.01)
*A61M 25/06* (2006.01)
(52) U.S. Cl.
CPC ............... *A61M 25/0662* (2013.01); *A61B 2017/00247* (2013.01); *A61B 2017/00336* (2013.01)
(58) Field of Classification Search
CPC ..... A61M 2025/0687; A61B 17/00234; A61B 17/3478; A61B 2017/00336; A61B 2017/00247
See application file for complete search history.

(56) References Cited

U.S. PATENT DOCUMENTS

| | | | |
|---|---|---|---|
| 5,499,975 A | 3/1996 | Cope et al. | |
| 6,029,672 A * | 2/2000 | Vanney | A61F 2/2493 128/898 |
| 8,485,969 B2 | 7/2013 | Grayzel et al. | |
| 2007/0225659 A1 | 9/2007 | Melsheimer | |
| 2008/0027380 A1 * | 1/2008 | Wholey | A61M 25/0662 604/104 |
| 2008/0269794 A1 * | 10/2008 | Spurchise | A61B 17/0057 606/191 |
| 2008/0306442 A1 | 12/2008 | Bardsley et al. | |
| 2012/0022575 A1 | 1/2012 | Mire | |
| 2012/0232658 A1 * | 9/2012 | Morgenstern Lopez | A61B 17/1757 623/17.16 |
| 2013/0184736 A1 | 7/2013 | Aman et al. | |

OTHER PUBLICATIONS

Halabi et al., "Aortic Access From the Vena Cava for Large Caliber Transcatheter Cardiovascular Interventions Pre-Clinical Validation," *Journal of the American College of Cardiology*, 61(16):1745-1746 (Apr. 23, 2013).
International Search Report and Written Opinion for related International Application No. PCT/US2014/060270, dated Jan. 14, 2015, 10 pages.

* cited by examiner

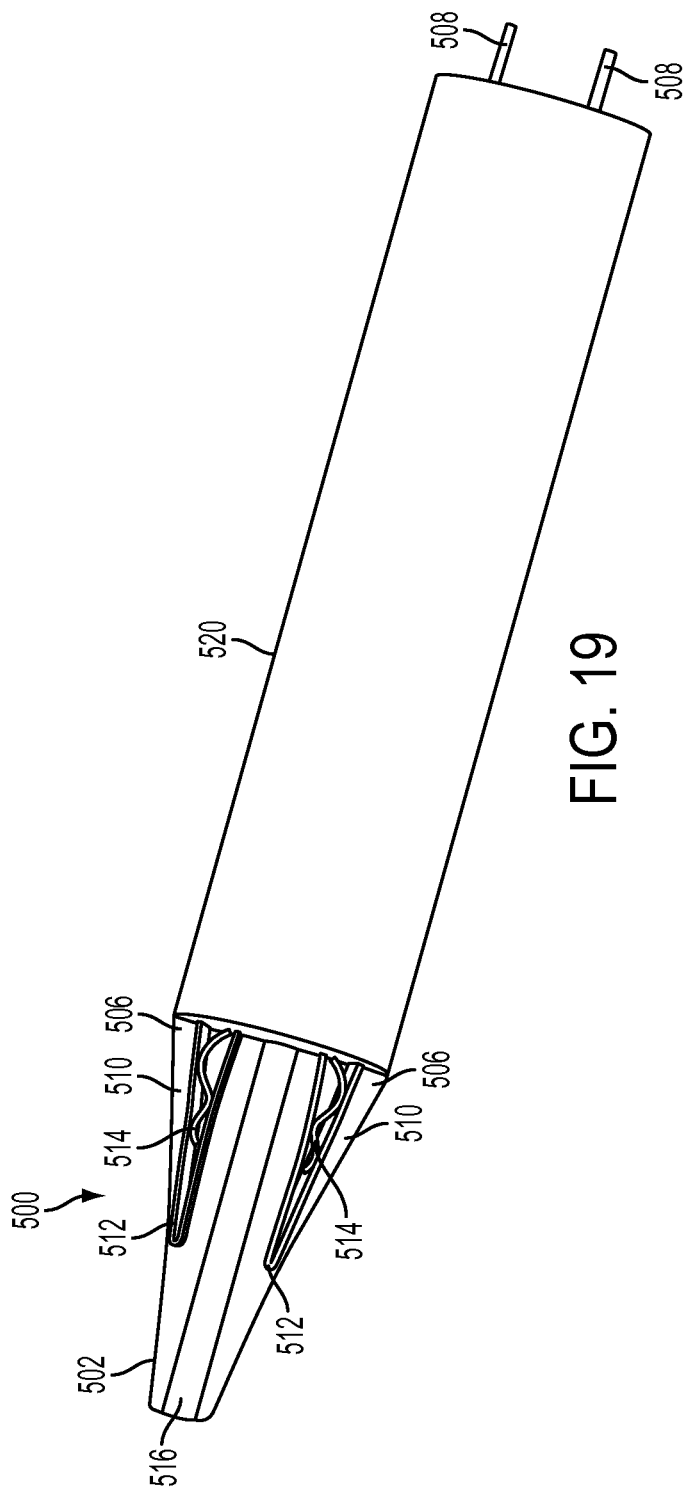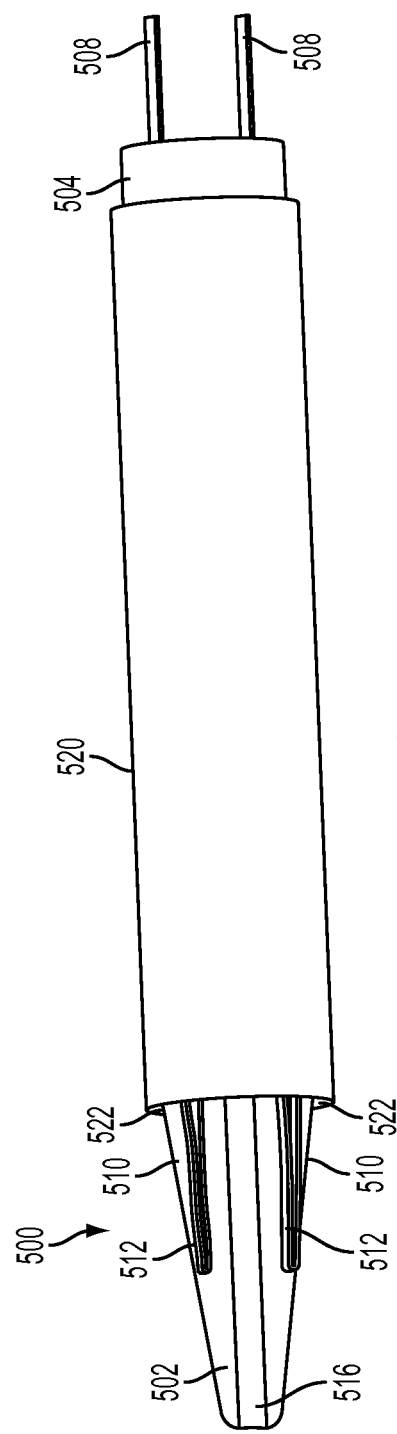

VASCULAR DILATORS

CROSS-REFERENCE TO RELATED APPLICATIONS

This application is the U.S. National Stage of International Application No. PCT/US2014/060270, filed Oct. 13, 2014, which was published in English under PCT Article 21(2), and which claims the benefit of U.S. Provisional Application No. 61/890,961, filed Oct. 15, 2013, and entitled "VASCULAR DILATORS," which is incorporated by reference herein in its entirety.

FIELD

This application is related to vascular dilators and introducer sheaths.

BACKGROUND

Catheter-based intravascular procedures typically require insertion of a vascular dilator followed by an introducer sheath. A conventional vascular introducer sheath 10, as illustrated in FIG. 1, has a vascular crossing profile, or diameter, necessarily wider than the accompanying vascular dilator 12, such that the dilator can be later retracted through the introducer sheath. This excess crossing profile of the introducer sheath is known to interfere with smooth advancement of the introducer sheath into a target blood vessel 14 or other chamber, and is known to cause tears in the target blood vessel, more commonly at or near the "trailing edge" 18 of the sheath 10, which refers to the portion of the distal end of the sheath that enters the vessel last when the device is inserted at an angle to the vessel, as in typical use. The "leading edge" 20 of the sheath 10, on the other hand, refers to the portion of the distal end of the sheath that enters the vessel first.

FIG. 2 shows an exemplary torn opening 16 in a vessel 14 caused by unequal crossing profiles of a conventional dilator 12 and introducer sheath 10, as well as a desired entry opening 22 having a smooth elliptical shape. As shown in FIG. 3, similar problems, such as puckering and tearing, can also occur during direct transthoracic or direct transmyocardial entry into the heart through a heart wall 24, such as for prosthetic heart valve implantation. The excess crossing profile in conventional intravascular systems is driven by the finite thickness of the wall of the introducer sheath, the limited flexibility of the introducer sheath, the required rigidity of the vascular dilator, and the requirement to withdraw the vascular dilator proximally through the sheath after delivery. Large-bore introducer sheaths, such as for structural heart interventions, tend to be necessarily thicker and more rigid and exacerbate these problems.

SUMMARY

Technology disclosed herein provides a reduced transition between a vascular dilator and the distal edge of an accompanying vascular introducer sheath. Disclosed dilators can be segmented into two or more primarily longitudinally extending parts, can have rigid circumferential or semi-circumferential leading shoulders to minimize the transition between the dilator and the distal sheath edge, and can contain internal recesses to allow sequential retraction of segments once the introducer sheath is delivered to a target chamber. Some dilators have radially adjustable shoulders and longitudinally movable mandrels to control the position of the adjustable shoulders. With this technology, vascular introducer sheaths can be introduced percutaneously into a broad range of diseased target vessels and chambers with reduced damage to the wall of the vessel or chamber, and with reduced damage to the distal end of the introducer sheath.

Some disclosed vascular dilators comprise a first segment and a second segment that are coupled together along an interface that extends primarily in the directions of a longitudinal axis of the dilator (i.e., the proximal and distal directions), such that the first segment and the second segment are slidable longitudinally relative to one another along the interface. Such dilators are configured for use with an introducer sheath, wherein the second segment can be retracted proximally through the introducer sheath alongside a proximal shaft of the first segment during a first stage, and then the first segment can be retracted proximally through the introducer sheath during a subsequent stage.

The dilators can comprise a tapered distal portion and a generally cylindrical shaft portion proximal to the tapered distal portion, with the tapered distal portion including a shoulder portion that extends at least partially around the circumference of the tapered distal portion to shield the distal end of the sheath. Each longitudinal segment, or some of the segments, can include a part of the shoulder portion.

In some embodiments, the shoulder extends less than 360° circumferentially around the dilator. For example, a first part of the shoulder portion on the first segment can extend less than 180° circumferentially and a second part of the shoulder portion on the second segment can extend less than 180° circumferentially. In some embodiments, each part of the shoulder extends 90° or less circumferentially and/or the total of all shoulder portions extends 180° or less circumferentially. In other embodiments, only one segment contains a shoulder to be applied by the user to the most "vulnerable" portion of the vascular access target, for example a non-circumferential shoulder that is aligned with the "trailing edge" of the vascular entry target.

The shaft portion of the first segment is engaged with a shaft portion of the second segment such that the first segment can be moved longitudinally relative to the second segment but non-longitudinal motion between the shaft portions of the first and second segments is restricted. The first segment can comprise a recess located at least partially within a tapered distal portion of the first segment, and the distal end portion of the second segment can be configured to deflect inwardly into the recess of the first segment during retraction of the second segment.

In some embodiments, a dilator further comprises a third segment coupled to the first and second segments along interfaces that extend primarily longitudinally, and the third segment is slidable longitudinally relative to the first and second segments along the interfaces. In such embodiments, the first, second, and third portions can each comprise a portion of a shoulder, and the shoulder can extend all the way around the dilator.

In some embodiments, the first segment can comprise a fully annular distal tip, or nosecone, that extends 360° circumferentially and defines a distal portion of a guidewire lumen passing through the dilator. The second segment can comprise a proximal portion of the guidewire lumen.

The dilators described herein can be used with an introducer sheath comprising a distal end portion that has a generally constant outer radius and at least some part of the distal end portion has an inner radius that increases moving distally toward a distal end of the introducer sheath.

An exemplary method of using a vascular dilator with an introducer sheath comprises advancing a first segment of the dilator distally relative to a second segment of the dilator and the introducer sheath, the first and second segments being engaged together along an interface that extends primarily in the proximal and distal directions, the introducer sheath being positioned around proximal shaft portions of the first and second segments; then retracting the second segment proximally through the introducer sheath alongside a shaft portion of the first segment; and then retracting the first segment proximally through the introducer sheath.

In some methods, retracting the second segment comprises causing a shoulder portion of the second segment to contact a distal end of the introducer sheath and thereby cause a distal portion of the second segment to deflect radially inwardly into a recess formed in the first segment, such that the shoulder portion of the second segment moves radially inwardly a sufficient distance to enter the introducer sheath. Similarly, retracting the first segment can comprise causing a shoulder portion of the first segment to contact a distal end of the introducer sheath and thereby cause a distal portion of the first segment to deflect radially inwardly a sufficient distance to enter the introducer sheath.

Some methods further comprise retracting a third segment proximally through the introducer sheath prior to retracting the first segment, the third segment being engaged to the first and second segments along interfaces that extend primarily in the proximal and distal directions.

Some methods further comprise initially inserting the vascular dilator and the introducer sheath into a blood vessel through a vessel wall or into a hearth through a heart wall, wherein the inserting is performed with a distal end of the introducer sheath positioned adjacent to a proximal surface of a shoulder of the dilator, the shoulder having a maximum radial dimension about equal to the outer radius of the introducer sheath. In some cases, the dilator and introducer sheath can be used to access an aorta from an inferior vena cava or to access a heart chamber through a heart wall.

Some exemplary vascular dilators comprise a main body having a tapered distal portion and a generally cylindrical proximal portion, at least one adjustable shoulder portion coupled to the tapered distal portion, and at least one mandrel extending through the main body and configured to affect a radial positioning of the adjustable shoulder portion. The mandrel can be moved proximally and distally relative to the main body and the shoulder portion. For example, when the mandrel is in a distal position, the shoulder portion is in a radially extended position, and when the mandrel is in a proximal position, the shoulder portion is allowed to move to a radially collapsed position. In the radially extended position, the shoulder portion can extend radially beyond the radial extent of the proximal portion of the main body, and in the radially collapsed position, the shoulder may not extend radially beyond the radial extend of the proximal portion of the main body.

In some embodiments, a biasing mechanisms, such as a spring element, can be positioned under each shoulder portion to bias the shoulder portion toward the radially expanded configuration. The biasing mechanism can be resiliently collapsed under radially inward pressure to allow the shoulder portion to move to the collapsed position.

Any number of shoulder portions and associated mandrels can be included.

Associated methods of using a vascular dilator with an introducer sheath comprise: (1) with a shoulder portion of the dilator being in a radially extended position to shield a distal end of the introducer sheath, moving a mandrel of the dilator proximally relative to the shoulder portion of the dilator and relative to the introducer sheath; and then (2) moving the dilator proximally relative to the introducer sheath with the shoulder portion of the dilator in a radially collapsed position such that the shoulder portion fits through the introducer sheath. Moving the mandrel proximally can causes the shoulder portion to move from the radially extended position to the radially collapsed position, and/or moving the dilator proximally relative to the introducer sheath can cause the shoulder portion interact with the distal end of the introducer sheath and thereby move from the radially extended position to the radially collapsed position.

Some methods further comprise moving the mandrel distally relative to the shoulder portion to cause the shoulder portion to move from the radially collapsed position to the radially extended position.

Some methods further comprise inserting the dilator and introducer sheath through an anatomical wall with the shoulder portion in the radially extended position to shield the sheath.

Some methods comprise using the dilator and introducer sheath to access an aorta from an inferior vena cava or to access a heart chamber through a heart wall.

The foregoing and other objects, features, and advantages of the disclosed technology will become more apparent from the following detailed description, which proceeds with reference to the accompanying figures.

BRIEF DESCRIPTION OF THE DRAWINGS

FIG. 19 is a perspective view of the dilator of FIG. 15 together with a vascular introducer sheath, with the distal portion of the dilator shown in cross-section.

FIG. 20 is a side view of the dilator and sheath of FIG. 19, with the distal portion of the dilator shown in cross-section, and with an adjustable shoulder portion of the dilator shown in a radially collapsed configuration.

DETAILED DESCRIPTION

Exemplary Vascular Dilators

Figure 4:
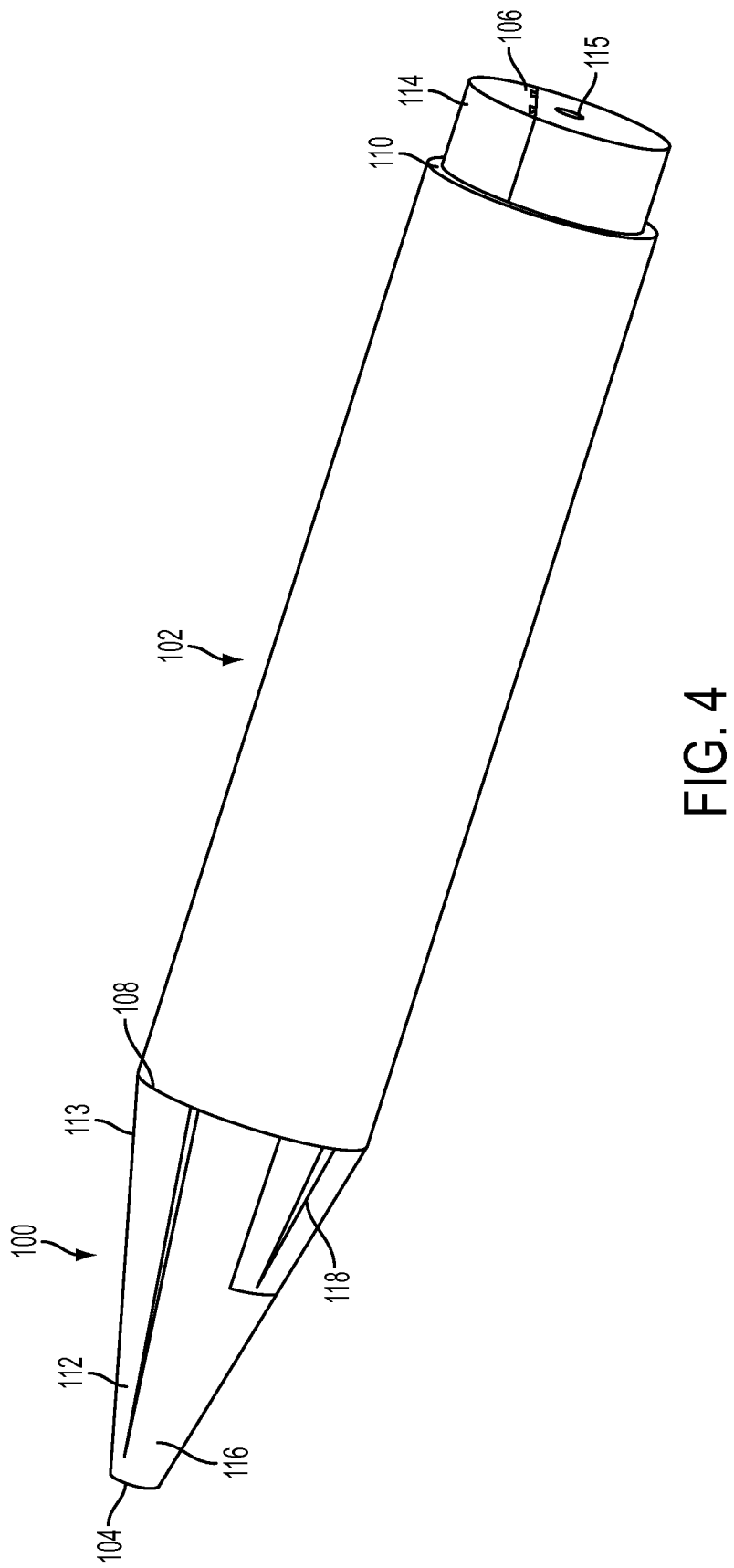
FIGS. 4 and 5 are perspective views of an exemplary segmented vascular dilator and an introducer sheath.
Figure 5:
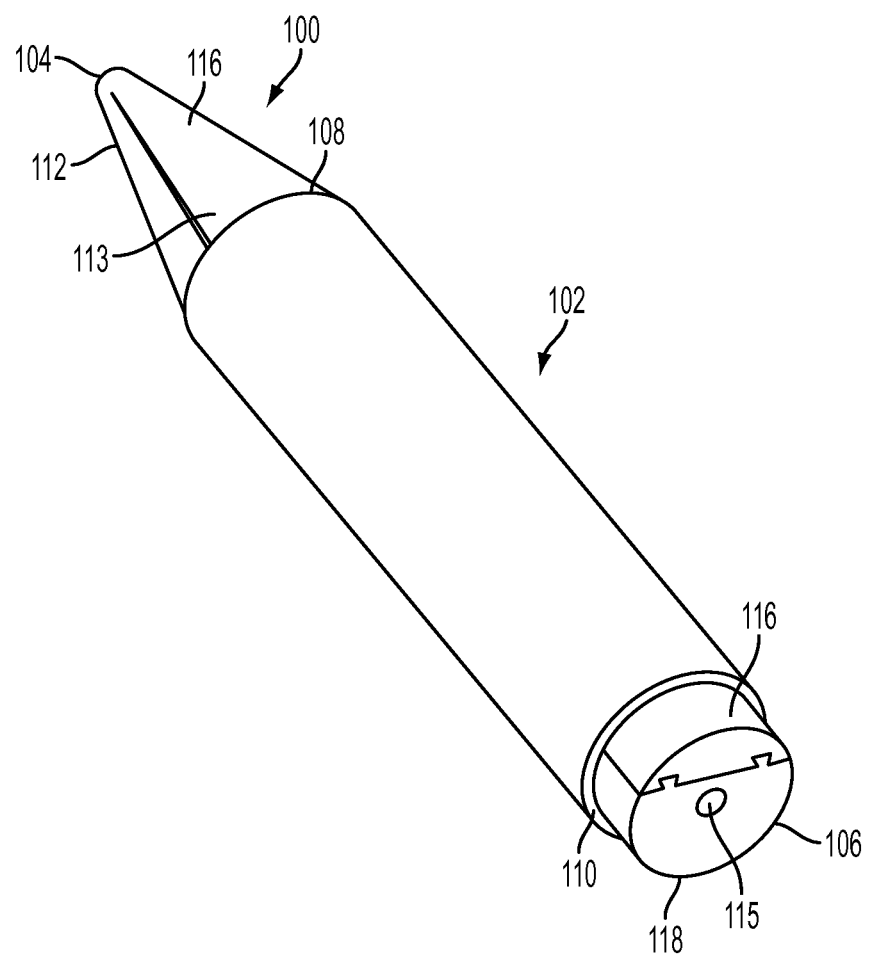

FIGS. 4 and 5 show an exemplary vascular dilator 100 and an exemplary introducer sheath 102. The dilator 100 and the sheath 102 are shown in an assembled configuration for insertion into a blood vessel, through a heart wall, or similar procedure. The dilator 100 has a distal end 104 and extends proximally through the sheath 102 toward a proximal end. The dilator 100 can have any length as needed for a particular procedure, and can terminate at a proximal hub, for example. The illustrated embodiment is shown truncated at a proximal end 106. Similarly, the sheath 102 has a distal end 108 and can extend proximally any length as needed, and can terminate at a proximal hub, for example. The illustrated embodiment is shown truncated at a proximal end 110 distal to the proximal end 106 of the dilator. The dilator 100 can also include a central guidewire lumen 115 extending along the length of the dilator.

The dilator 100 has a frustoconical shaped distal tapered portion 112 for penetration and dilation of a vessel wall, heart wall, or the like, and a generally tubular shaft 114 extending proximally from the tapered portion through the sheath 110. The external surface of the tapered portion 112 forms a shoulder 113 adjacent to the distal end 108 of the sheath 102 to shield the distal end of the sheath and create a smooth transition with the outer diameter of the sheath. The maximum outer radius of the shoulder 113 can be about equal to the outer radius of the sheath 102. In other embodiments, the maximum outer radius of the shoulder 113 can be between the inner radius of the sheath 102 and the outer radius of the sheath 102. In still other embodiments, the maximum outer radius of the shoulder 113 can be slightly larger than the outer radius of the sheath 102.

The shoulder 113 can extend around a portion of the circumference of the dilator, and can be broken into plural shoulder portions. For example, the maximum outer diameter of the dilator 100 at the shoulder 113 can be about equal to the outer diameter of the sheath 102, while the outer diameter of the dilator at other circumferential portions lacking a shoulder can be about equal to the inner diameter of the sheath 102.

The dilator 100 comprises a first segment 116 (FIGS. 6 and 7) and a second segment 118 (FIGS. 8 and 9) that mate together and can be independently moved in the proximal and distal directions (also referred to as the "longitudinal" directions) or moved in unison. The first segment 116 and the second segment 118 can each include part of the distal tapered portion 112 and part of the proximal shaft 114, such that the dilator 100 is generally longitudinally segmented.

Segmentation of the dilator 100 allows for independent retraction of each segment through the sheath 102. The two segments can initially be fixed together during insertion, then moved in the longitudinal directions independently for retraction. For example, during retraction from a vessel, the second segment 118 can be initially retracted through the sheath 102 first, and then second segment 116 can be subsequently retracted through the sheath.

The distal portion 131 of the first segment 116 includes a nosecone 119 forming the distal-most portion of the guidewire lumen 115, and an internal recess 120 (FIG. 6) proximal of the nosecone 119. The recess 120 allows the distal portion 122 of the second segment 118 to deflect radially inwardly into the recess 120 during retraction to reduce its radial dimensions for passage through the sheath 102.

The first and second segments 116, 118 can be held together via an engagement that allows for at least some degree of longitudinal movement relative to each other, but restricts non-longitudinal movement relative to each other. In some embodiments, a dovetail-type engagement and/or interlocking of complementary components of the first and second components 116, 118 can be used that allows for relative longitudinal sliding but prevents non-longitudinal separation. For example, the first segment 116 can include female grooves 130 (FIG. 6) that extend longitudinally along the shaft portion 132 of the first segment, and the second segment 118 can include corresponding male rails 134 (FIG. 9) in the shaft portion 136 of the second segment, such that the rails 134 can slide longitudinally in the grooves 130. The rails 134 and grooves 130 can interlock, using a dovetail-like configuration, to prevent the two segments from separating apart radially or laterally from each other. In other embodiments, the first segment 116 can include male rails and the second segment can include female grooves, or the first and second segments can include one or more rails and one or more grooves that mate with each other.

Figure 6:
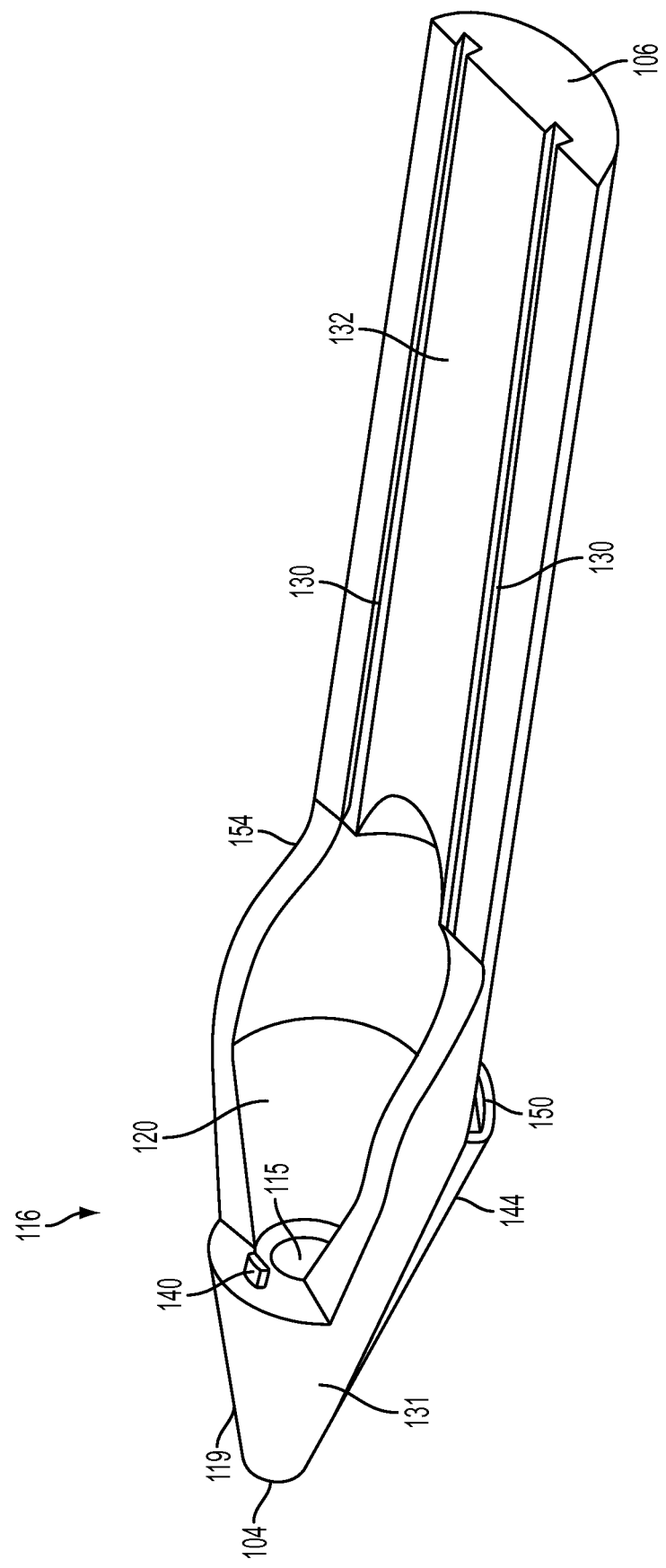
FIGS. 6 and 7 are perspective views of one segment of the dilator of FIG. 4.
Figure 7:
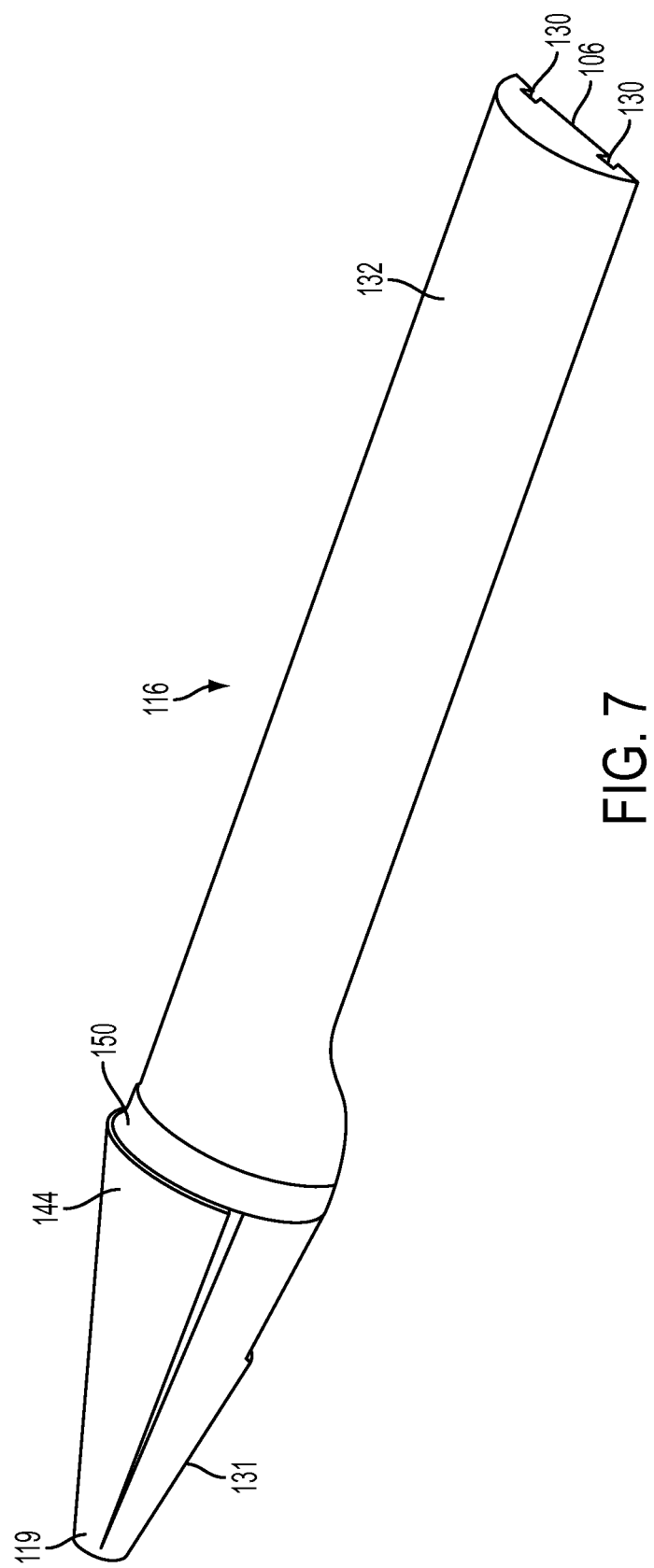

In other embodiments, various alternative types of suitable engagement mechanisms can be included instead of or in addition to the rails and groove described above. For example, pins or pegs can be used to help align the two segments and restrict non-longitudinal motion. As shown in FIG. 6, for example, the distal portion 131 of the first segment 116 can include a pin 140 that extends proximally and is configured to mate with a hole (not shown) in the distal tip 142 of the second segment 118 to restrict the second segment from separating or collapsing in the non-longitudinal directions relative to the first segment while they are engaged together in the insertion configuration shown in FIGS. 4 and 5. Distal motion of the first segment 116 relative to the second segment 118 causes the pin 140 to disengage from the second segment, allowing the distal portion 122 of the second segment to deflect radially inwardly into the recess 120 of the first segment for retraction of the second segment through the sheath 102. Any number of such pins or similar registration features can be included in different embodiments.

Figure 1:
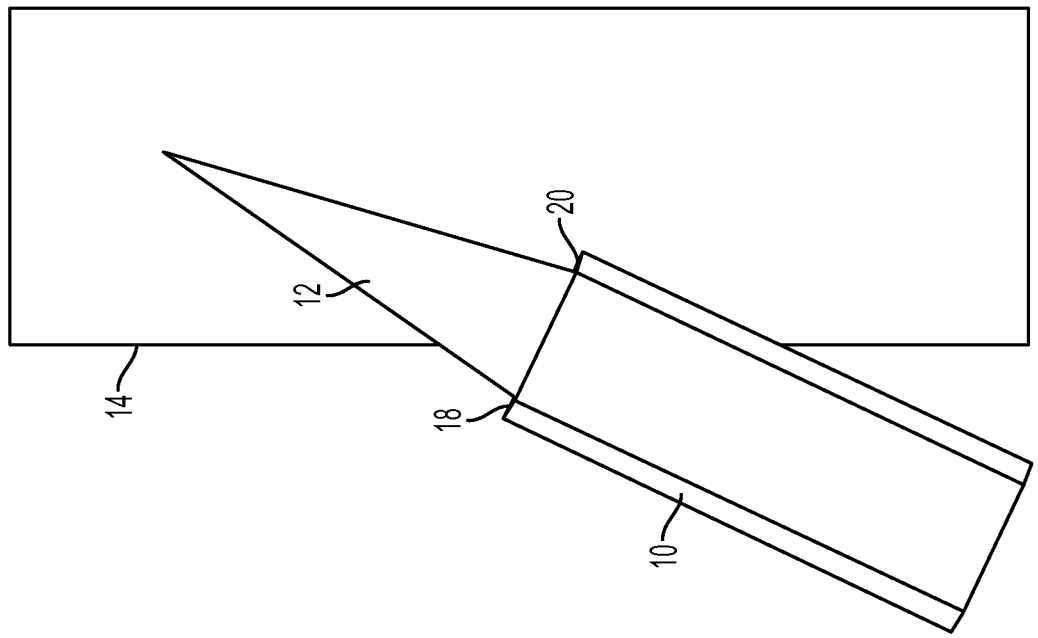
FIG. 1 shows a conventional vascular dilator and introducer sheath entering a blood vessel.
Figure 8:
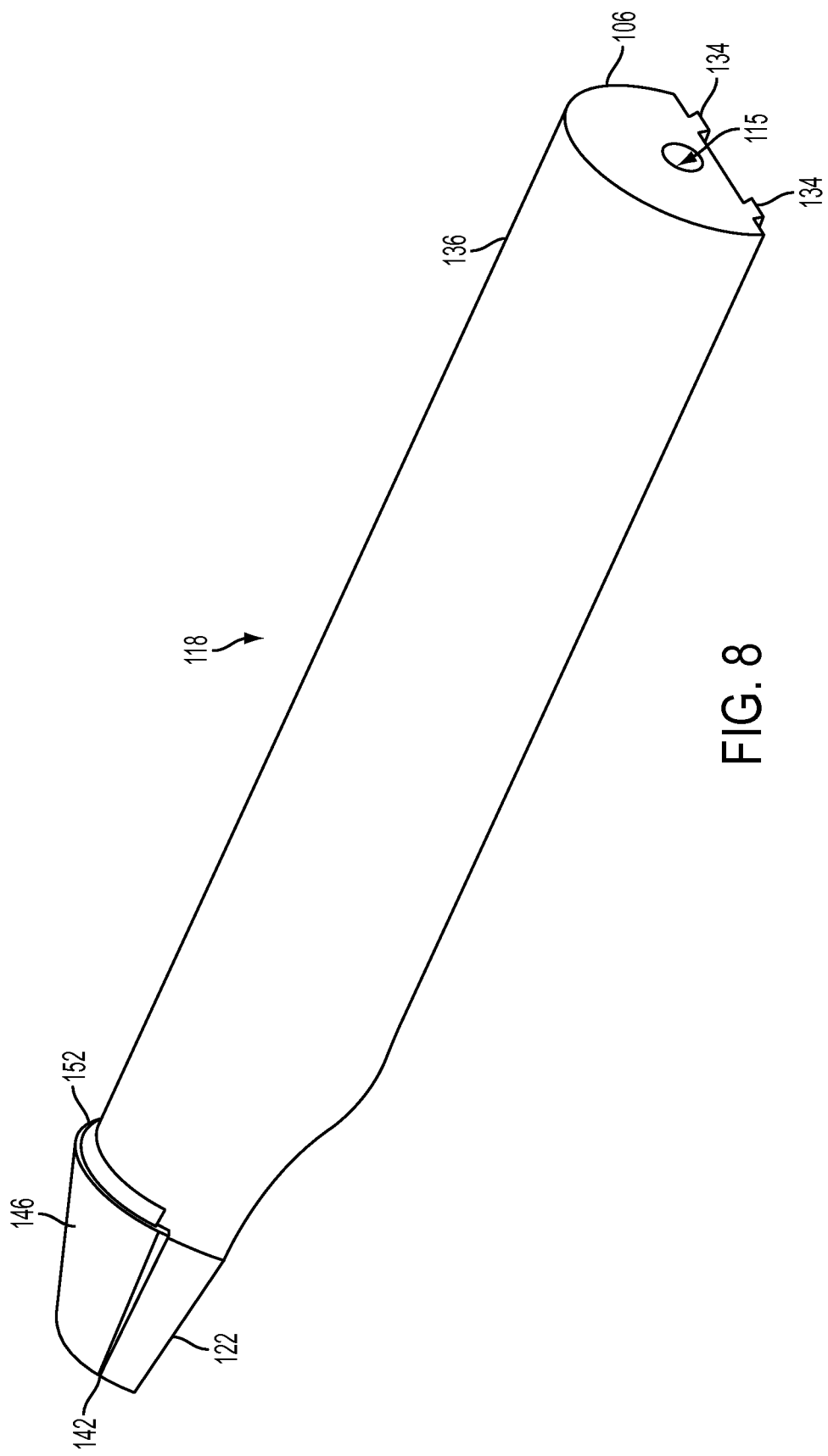
FIGS. 8 and 9 are perspective views of another segment of the dilator of FIG. 4.
Figure 9:
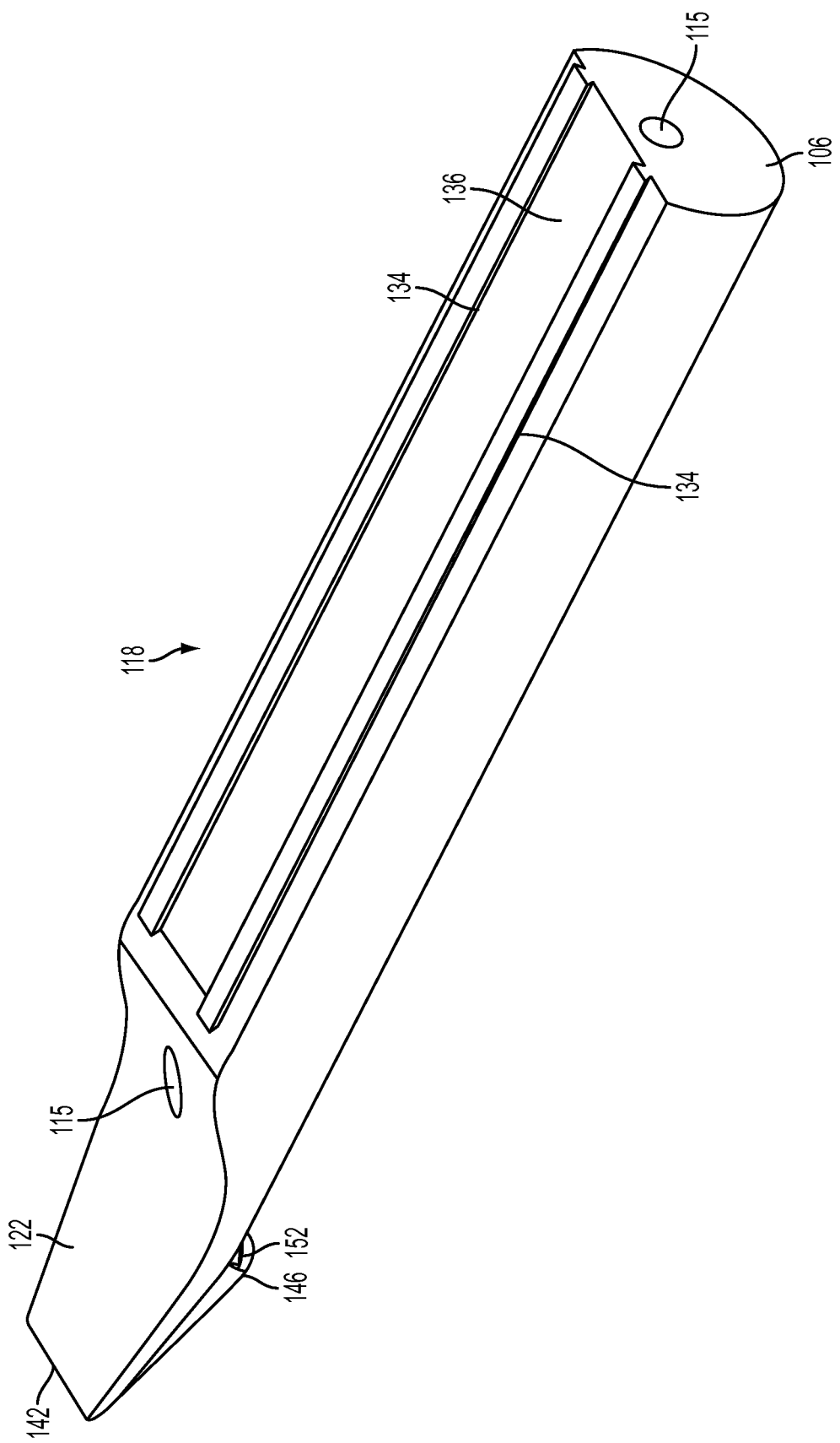

The shoulder 113 of the dilator 100 can be segmented into discrete circumferential portions. The first segment 116 can include a first shoulder portion 142 (FIG. 7) and the second segment 118 can include a second shoulder portion 144 (FIG. 8). The first and second shoulder portions 142, 144 can extend circumferentially about the dilator 100 less than 180° each, such as less than or equal to 150° each, less than or equal to 120° each, less than or equal to 90° each, and/or less than or equal to 75° each. In some embodiments, the first shoulder portion 142 can have a greater or lesser circumferential dimension than the second shoulder portion 144. For example, the dilator segment that is configured to be positioned adjacent to the trailing edge 18 of the sheath (see FIG. 1), where maximum damage to the vessel wall is most likely to occur due to an uneven transition between the dilator and the sheath, can comprise a larger shoulder portion (greater circumferential dimension) relative to the shoulder portion of the dilator segment that is configured to be positioned adjacent to the leading edge 20 of the sheath, where the least damage to the vessel wall occurs. Dilator segments having a shoulder portion that extends over less than 180° and/or over less than the maximum circumferential dimension of the particular segment allows each segment to have a maximum dimension perpendicular to the longitudinal directions that is less than the inner diameter of the sheath 102, such that each of the segment fits through the inner diameter of the sheath 102 during retraction.

The shoulder portions 144, 146 can include peripheral inclined surfaces 150, 152, respectively, on the proximal side of the shoulder that help the segments deflect radially inwardly during retraction to fit into the sheath 102. The inclined surfaces 150, 152 can have various geometries that transition from the greater radial dimension of the shoulder 144, 146 to the reduced radial dimension of the shaft portion 132, 136 of the respective segment. For example, the inclined surfaces 150, 152 can be concave, convex, linear, or a combination such shapes. The angle between the inclined surfaces 150, 152 and the outer surfaces of the shafts 132, 136, respectively, is generally greater than 90° to facilitate inward deflection of the segments during retraction when the inclined surfaces are flat. When the second segment 118 is retracted, for example, the shoulder portion 146 initially has a greater radial dimension that the inner lumen of the sheath 102, such that shoulder portion 146 contacts the distal circumferential end 108 of the sheath 102. However, the inclined surface 152 of the shoulder portion 146 can contact the distal end 108 of the sheath 102 first when the second segment 118 is retracted, which can cause the distal portion 122 of the second segment 118 to deflect radially inwardly enough to allow the shoulder portion 146 fit into and slide through the inner lumen of the sheath 102 without undue stretching or damage to the sheath. The sheath 102 can further have some degree of elasticity and flexibility to assist in this retraction process.

The first and second segments 116, 118 of the dilator 100 can comprise any suitable material that provides sufficient rigidity and flexibility. Exemplary materials include high density polyethylene (HDPE), high molecular weight polyethylene (HMWPE), high molecular weight polyurethane (HMWPU), and/or polypropylene. In some embodiments, the various portions of the dilator can be coated with silicone and/or other materials to reduce friction and/or serve other purposes.

Figure 2:
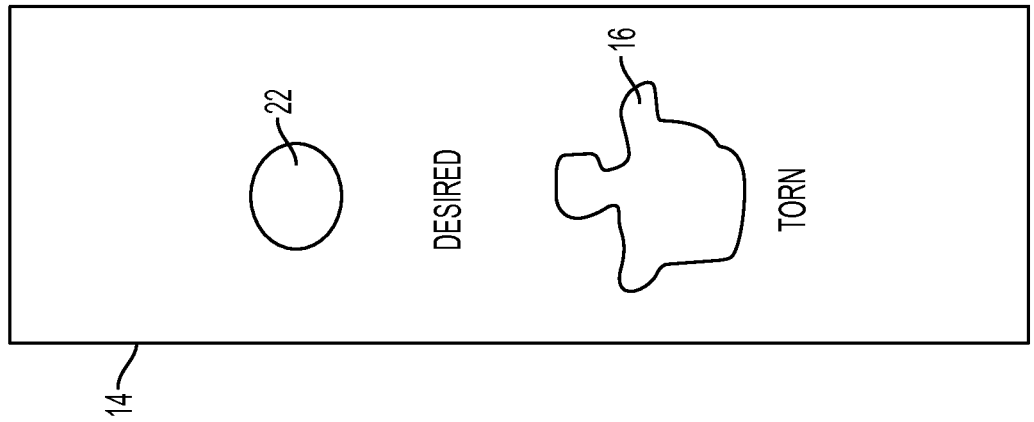
FIG. 2 illustrates a blood vessel having a torn opening caused by the device of FIG. 1, in comparison with a desired opening.

An exemplary method of using the dilator 100 is as follows. A guidewire is initially inserted through a wall of a target blood vessel and into the vessel. The dilator 100 and sheath 102, in the configuration shown in FIGS. 4 and 5, can then be threaded over the guidewire, with the guidewire passing through the guidewire lumen 115 of the dilator. As the dilator 100 and sheath 102 advance distally over the guidewire, the distal end 104 of the dilator passes through the wall of the vessel first. The gradually increasing diameter of the distal portion 112 of the dilator causes the opening in the vessel wall to gradually increase in size. As the shoulder 113 of the dilator passes through the wall of the vessel, the smooth transition between the shoulder 113 and the distal end of the sheath 102 allows the distal end of the sheath to enter through the vessel wall without tearing the opening, as shown in FIG. 2. The dilator 100 and sheath 102 are then advanced through the vessel as needed to dilate the vessel and/or accomplish additional procedures.

Once vessel dilation and/or any other procedures are completed with the dilator 100, the dilator can be retracted proximally out of the vessel through the sheath 102. The first segment 116 can be advanced distally relative to the second segment 118 and the sheath 102 within the vessel. Such advancement of the first segment can be accomplished with the sliding engagement of the rails 134 within the complimentary interlocking grooves 130, for example. The distal advancement of the first segment 116 can be sufficient to dis-engage the pin 140 from the corresponding hole in the second segment 118 and sufficient to position the distal portion 122 of the second segment adjacent to the recess 120 in the first segment 116 such that the distal portion 122 can deflect into the recess 120.

From this position, the second segment 118 can then be retracted proximally relative to first segment 116 and the sheath 102. Such retraction of the second segment 118 causes the shoulder portion 146 of the second segment 118 to contact the distal end 108 of the sheath 102 and thereby deflect the distal portion 122 of the second segment radially inwardly, with the assistance of the inclined surface 152. Once the distal portion 122 of the second segment 118 is deflected sufficiently inward, the shoulder portion 146 can enter the inner lumen of the sheath 102 allowing the second segment 118 to slide proximally along the guidewire through the sheath alongside of the proximal shaft portion 132 of the first segment 116, and eventually out of the vessel and/or out of the proximal end of the sheath. To provide more room within the sheath 102 for the distal portion 122 of the second segment 118 to slide alongside the shaft portion 132 of the first segment 116, the shaft portion 132 of the first segment can be minimized in cross-sectional profile, such as at least smaller than the shaft portion 136 of the second segment 118, as is shown in FIG. 5.

With the second segment 118 thus removed, the first segment 116 can then be retracted proximally relative to the sheath 102. Such retraction of the first segment 116 causes the shoulder portion 144 of the first segment 116 to contact the distal end 108 of the sheath 102 and thereby deflect the distal portion 131 of the first segment radially inwardly, with the assistance of the inclined surface 150. For example, the distal portion 131 of the first segment can bend primarily at a necked region 154 (FIG. 6) having a reduced cross-sectional area at the proximal end of the recess 120 adjacent to the shaft portion 132. Once the distal portion 131 of the first segment 116 is deflected sufficiently inward, the broad shoulder portion 144 can enter the inner lumen of the sheath 102, allowing the first segment 116 to slide proximally along the guidewire through the sheath and out of the vessel and/or out of the proximal end of the sheath.

Once the entire dilator 100 is retracted out of the vessel and/or out of the sheath 102, the sheath can be retracted out of the vessel and the opening in the vessel wall can be repaired.

Figure 10:
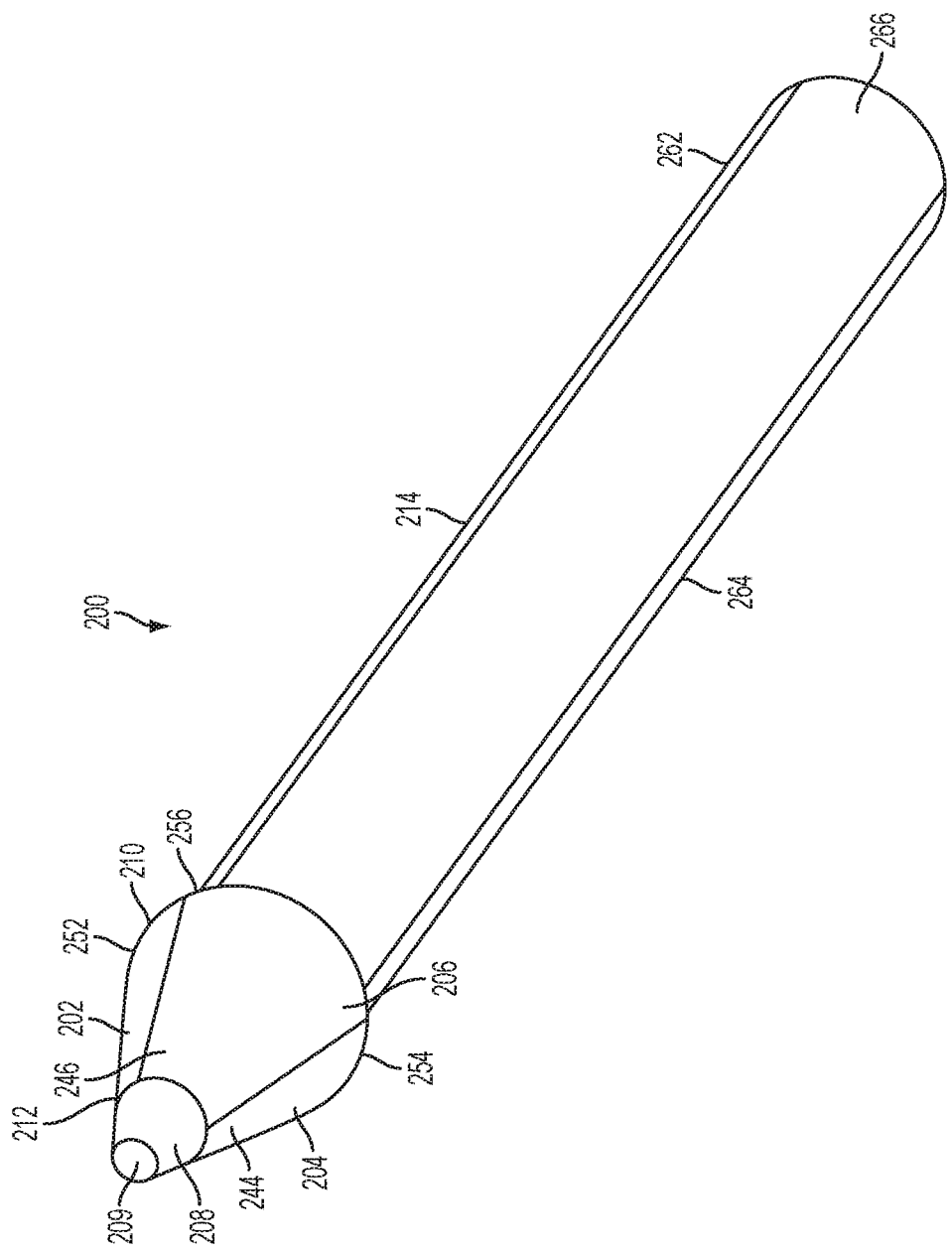
FIG. 10 is a perspective view of another exemplary segmented vascular dilator.
Figure 11:
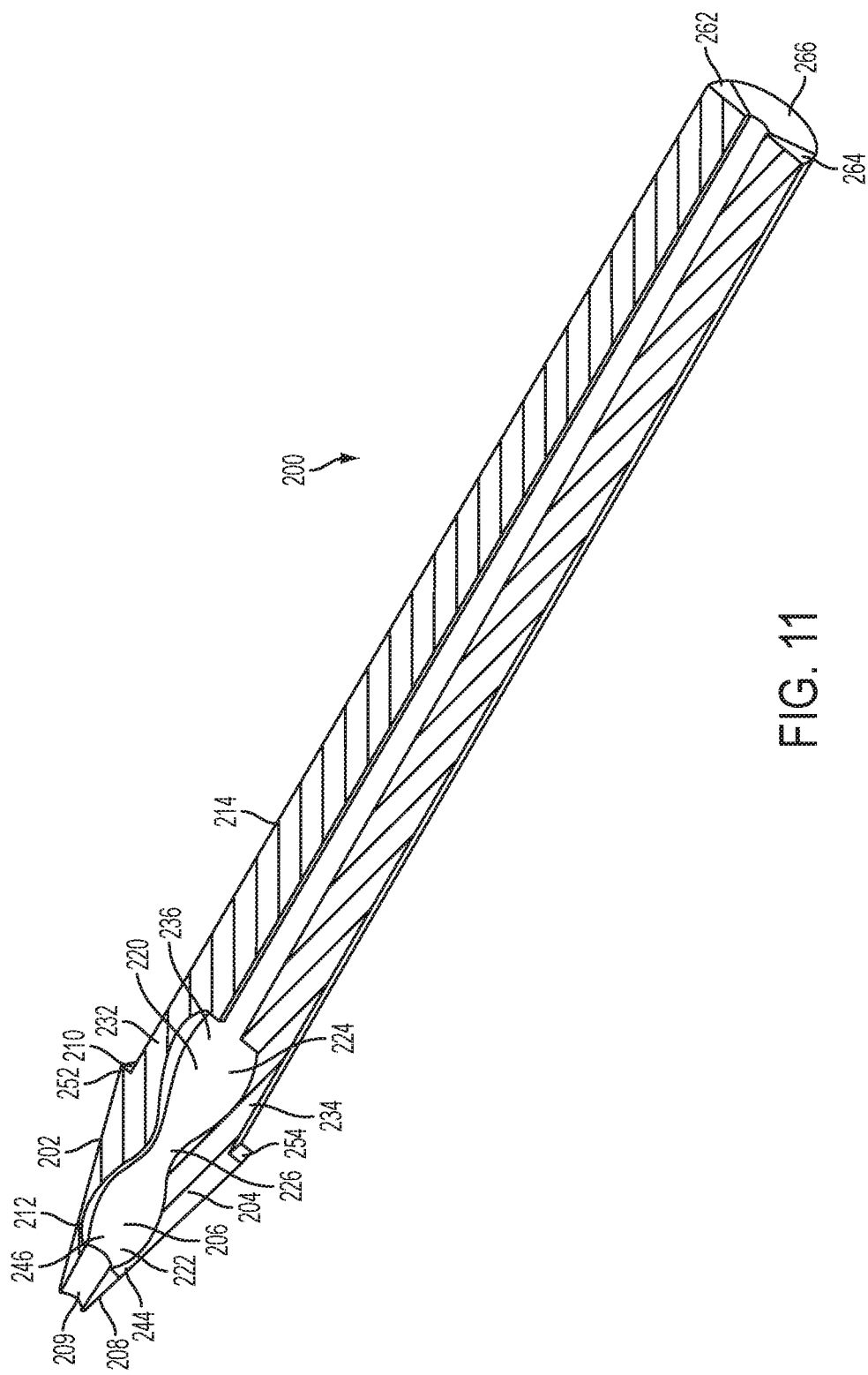
FIG. 11 is a perspective cross-sectional view of the dilator of FIG. 10, taken along its longitudinal axis.

FIGS. 10 and 11 show another exemplary segmented dilator 200 having three independently retractable segments that functions similarly to the dilator 100. The introducer sheath is not shown in these figures for clarity. A first segment 202 includes a distal nosecone 208 and defines the distal end of the dilator 200. The second segment 204 and third segment 206 can be similar in structure to each other, each terminating at a distal end proximal to the nosecone 208. Each of the three segments can extend less than 180° circumferentially and all three segments can extend proximally to a hub having actuators for moving the three segments longitudinally independently.

The outer surface of dilator 200 can include an external shoulder 210 extending up to 360° circumferentially, with each of the three segments forming a portion of the shoulder.

The dilator 200 includes a tapered distal portion 212 that includes the shoulder 210, and a generally cylindrical shaft portion 214 proximal to the shoulder 210. Each of the three segments 202, 204, 206 can comprise less than 180° circumferentially of the entire dilator 200, such as each segment comprising about 120°, or the first segment comprising between 120° and 180° with the second and third segments comprising between 90° and 120°, or other proportions and configurations.

Though not shown, the three segments 202, 204, 206 can be engaged with each other along the shaft portions 214 with engagement features that allow for at least some degree of longitudinal movement relative to one another, but restrict non-longitudinal movement relative to one another. In some embodiments, dovetail-type engagement features, like those shown with respect to the dilator 100, can be employed between each mating pair of surfaces in the shaft portion 214 (e.g., three sets of mating surfaces). Other types of suitable engagement mechanisms can also be used to allow for relative longitudinal sliding of the three segments but prevent non-longitudinal separation.

In addition, or alternatively, the distal tips of the second and/or third segments 204, 206 can be engaged with the proximal surface of the nosecone 208 with pin type engagements, similar to the pin 140 (FIG. 6) of the dilator 100, that restrict non-longitudinal motion of the distal ends of the second and third segments when engaged.

The three segments of the dilator 200 can form an enclosed internal recess 220 that extends from the nosecone 208 proximally into the shaft portion 214, as shown in FIG. 11. The recess 220 can be defined by all three of the segments in part. The recess 220 can form part of the guidewire lumen 209 and also allow for inward deflection of the distal ends of the segments during retraction, like with the recess 120 in the dilator 100. As shown in FIG. 11, the recess 220 can have the general shape of an hourglass, with expanded distal and proximal portions 222, 224 and a necked intermediate portion 226.

The first, second, and third segments 202, 204, 206 can have relatively thin portions 232, 234, 236 just proximal to the shoulder 210 at a longitudinal location even with the proximal portion 224 of the recess 220. The thin portions 232, 234, 236 allow the distal portion of each segment to flex radially inwardly during retraction through an introducer sheath. Like with the dilator 100, the shoulder 210 of the dilator 200 can include an inclined proximal surface to help cause radially inward deflection when each segment is retracted through the sheath.

The first, second, and third segments 202, 204, 206 of the dilator 200 can comprise any suitable material that provides sufficient rigidity and flexibility. Exemplary materials include HDPE, HMWPE, HMWPU, and polypropylene. In some embodiments, the various portions of the dilator 200 can be coated with silicone or other materials to reduce friction and/or serve other purposes.

An exemplary method of using the dilator 200 is as follows. A guidewire is initially inserted through a wall of a target blood vessel and into the vessel. The dilator 200, in the configuration shown in FIG. 10, with an introducer sheath covering the shaft 214 and abutting the shoulder 210, can then be threaded over the guidewire, with the guidewire passing through the guidewire lumen 209 of the dilator. As the dilator 200 and sheath advance distally over the guidewire, the distal end of the nosecone 208 passes through the wall of the vessel first. The gradually increasing diameter of the distal portion 212 of the dilator causes the opening in the vessel wall to gradually increase in size. As the shoulder 210 of the dilator passes through the wall of the vessel, the smooth transition between the shoulder 210 and the distal end of the sheath allows the distal end of the sheath to enter through the vessel wall without tearing the opening, as shown in FIG. 2. The dilator 200 and sheath are then advanced through the vessel as needed to dilate the vessel and/or accomplish additional procedures.

Once vessel dilation and/or any other procedures are completed with the dilator 200, the dilator can be retracted proximally out of the vessel through the sheath. The first and second segments 202, 204 can be initially advanced distally (in unison, or one at a time) relative to the third segment 206 and the sheath. Such advancement of the first and second segments can be accomplished with the sliding engagement of the rails within the grooves along the shaft portion 214, for example. The distal advancement of the first and second segments 202, 204 can be sufficient to dis-engage a pin-and-hole engagement between the distal end of the third segment 206 and the proximal side of the nosecone 208. The longitudinal advancement of the first and second segments 202, 204 can be sufficient to position the distal portion 246 of the third segment 206 adjacent to the distal portion 222 of the recess 220 and to position the shoulder portion 256 of the third segment 206 adjacent to the proximal portion 224 of the recess 220.

This small distal advancement of the first and second segments 202, 204 allows the distal portion 246 of the third segment 206 to deflect into the distal portion 222 of the recess 220 and allows the shoulder portion 256 of the third segment 206 to deflect into the proximal portion 224 of the recess during subsequent retraction of the third segment 206 relative to the sheath. During retraction of the third segment 206, the shoulder portion 256 contacts the distal end of the sheath, causing inward deflection sufficient to allow the shoulder portion 256 to enter the lumen of the sheath, with the assistance of the inclined proximal surface of the shoulder, and such that the entire third segment 206 can be retracted out through the sheath. To provide more room within the sheath for the shoulder portion 256 of the third segment 206 to slide alongside the shaft portions 262, 264 of the first and second segments 202, 204, the shaft portions 262, 264 of the first and second segments can be minimized in cross-sectional profile, such that they are at least smaller than the shaft portion 266 of the third segment 206. Similarly, the second shaft portion 264 can be smaller than the first shaft portion 262 to allow more room for the shoulder portion 254 of the second segment within the sheath.

With the third segment 206 thus removed, the second segment 204 can then be retracted proximally relative to the first segment 202. Such retraction of the second segment 204 can be sufficient to disengage the any pin-and-hole type engagement between the distal end of the second segment and the proximal side of the nosecone 208. As the shoulder portion 254 of the second segment 204 contacts the distal end of the sheath, the distal portion of the second segment deflects inwardly into the recess 220, with the distal end 214 deflecting into the distal portion 222 of the recess and the shoulder region 254 deflecting into the proximal portion 224 of the recess. Once the distal portion of the second segment 204 is deflected sufficiently inward, the broad shoulder portion 254 can enter the inner lumen of the sheath, allowing the second segment 204 to slide proximally along the guidewire through the sheath alongside the shaft portion 262 of the first segment 202.

With the first and second segments 204, 206 thus removed, the first segment 202 can be retracted proximally through the sheath, with the distal portion of the first segment deflecting inwardly as needed as the shoulder portion 252 contacts the distal end of the sheath. Once the entire dilator 200 is retracted through the sheath, the sheath can be retracted out of the vessel and the opening in the vessel wall can be repaired.

Figure 12:
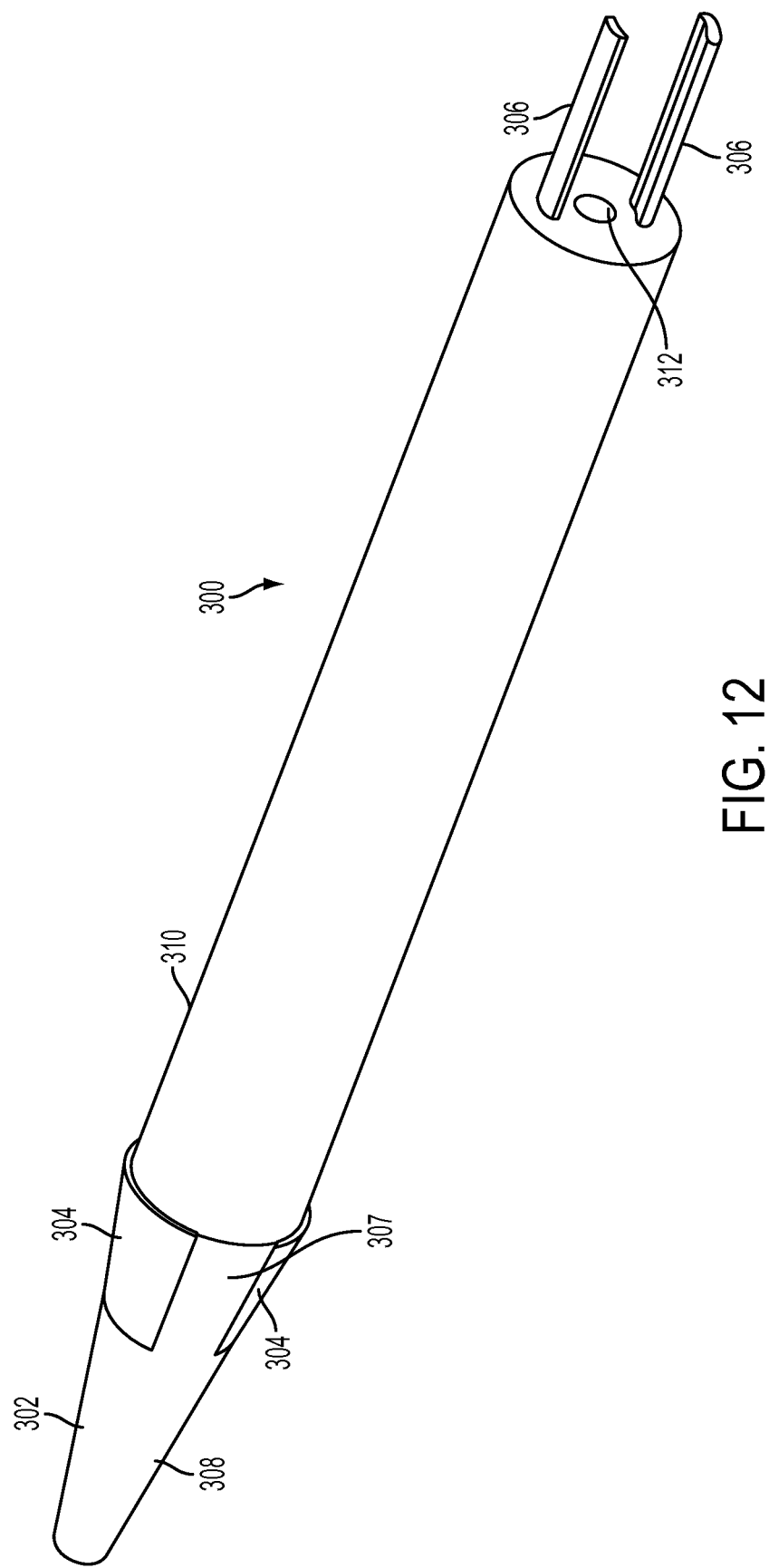
FIG. 12 is a perspective view of yet another exemplary vascular dilator.
Figure 13:
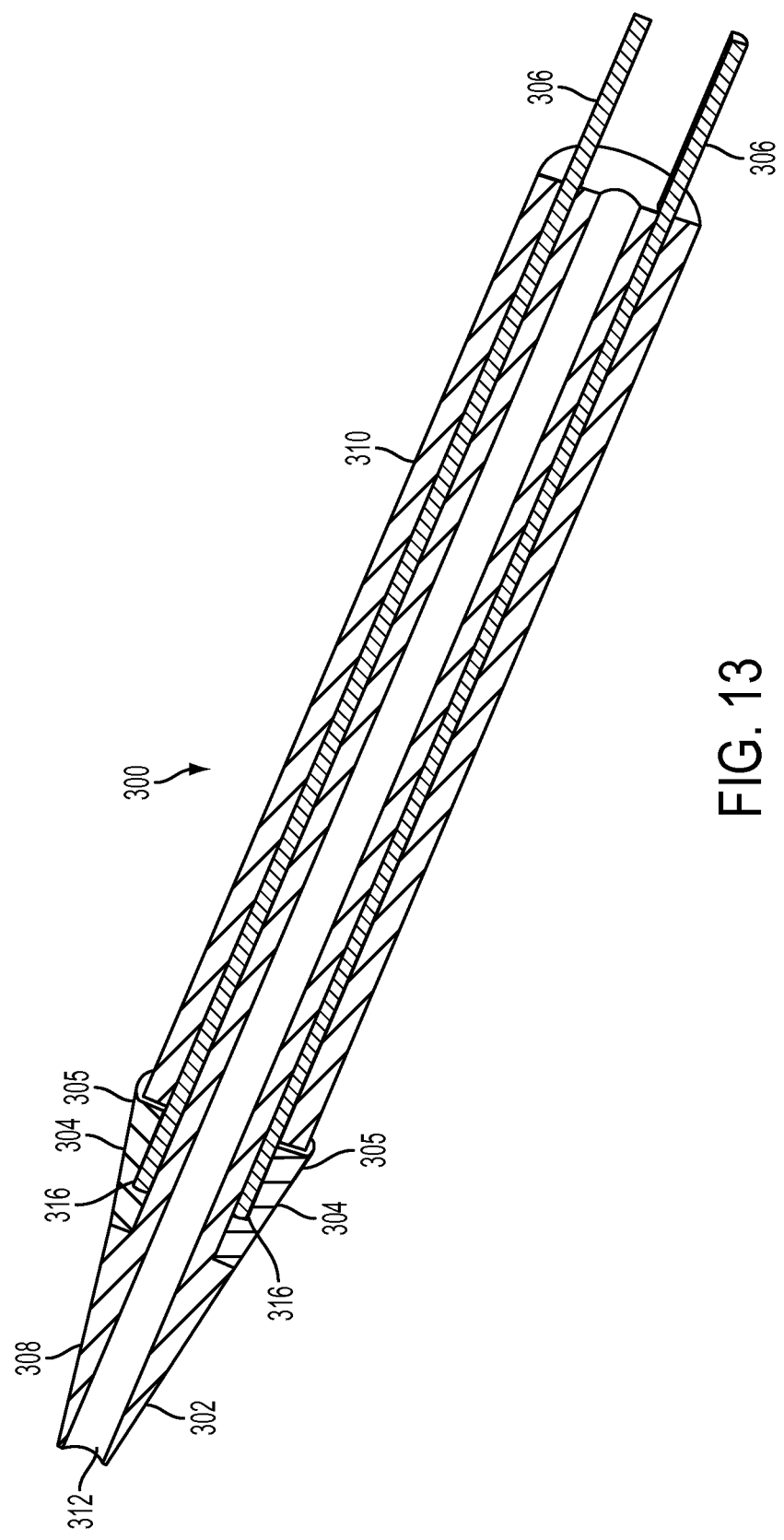
FIG. 13 is a perspective cross-sectional view of the dilator of FIG. 12, taken along its longitudinal axis.

FIGS. 12 and 13 show another exemplary dilator 300 comprising a rigid main body 302, adjustable shoulder portions 304, and mandrels 306 for adjusting the shoulder portions 304. The main body includes a distal portion 308 and a proximal shaft portion 310. An introducer sheath is not shown in these figures for clarity, though an introducer sheath would be positioned around the shaft portion 310 and abutting the shoulder portions 304. A guidewire lumen 312 extends through the length of the main body 302. The dilator 300 can comprise two, three, four, or more shoulder portions 304, with a corresponding number of mandrels 306.

In the embodiment shown in FIG. 12, the two shoulder portions 304 are located on opposite sides of the dilator and extend about less than the entire circumference of the dilator. Each shoulder portion can extend circumferentially less than 180°, less than 150°, and/or less than 120°, but have sufficient circumferential size to provide a smooth transition between the dilator and the sheath.

Between the shoulder portions 304, the main body 302 of the dilator can have a smooth transition 307 from the cone-like distal portion 308 to the shaft portion 310, such that no shoulder is present at these transitions 307.

The mandrels 306 can slide longitudinally to cause the shoulder portions 304 to move between a radially collapsed position and a radially extended position. For example, an actuator at a proximal hub outside the vessel can control longitudinal motion of the mandrels 306 relative to the rest of the dilator 300. In the radially collapsed position, the mandrels 306 are slid proximally relative to the rest of the dilator, causing the distal ends 316 of the mandrels to move out from under a flexible proximal portion 305 of the shoulder portions 304, allowing the proximal portions 305 of the shoulder portions to collapse or bend inwardly. For example, in the radially collapsed position, the maximum radial extent of the shoulder portions 304 can be about equal to, or less than, the radius of the shaft portion 310 of the main body 302.

In the radially extended position (shown in FIGS. 12 and 13), the mandrels 306 are slid distally relative to the rest of the dilator 300 such that the distal ends 316 of the mandrels 306 move under the proximal portions 305 of the shoulder portions, causing the proximal portions 305 of the shoulder portions to move or expand radially outwardly beyond the diameter of the shaft portion 310.

During insertion into a vessel, the shoulder portions 304 can be positioned in the radially extended position, such that the shoulder portions 304 extend radially beyond the diameter of the shaft portion 310, such as about even with the outer diameter of the sheath to provide a smooth transition and minimize tearing of the vessel wall during insertion.

To remove the dilator from the vessel through an introducer sheath, the mandrels 306 can be moved proximally relative to the rest of the dilator 300 to cause the proximal portions 305 of the shoulder portions 304 to move radially inwardly to the radially collapse position. With the shoulder portions 304 in the collapsed position, the dilator 300 has little or no shoulder, presenting a smooth, transition between the tapered distal portion 308 and the shaft portion 310 all the way around the dilator. This allows the dilator 300 to be retracted through the sheath.

In some embodiments, the distal end of the sheath contacts the shoulder portions 304 and forces them to collapse radially inwardly into voids under the proximal portions 305 of the shoulder portions formed by the absence of the distal ends 316 of the mandrels underneath. In such embodiments, moving the mandrels 306 proximally out from under the shoulder portions may not cause the shoulder portions to collapse inwardly, and instead the shoulder portions remain extending naturally radially outwardly until the distal end of the sheath exerts a radially inward force on them, causing them to deflect inwardly.

In other embodiments, moving the mandrels 306 proximally directly causes the proximal portions 305 of the shoulder portions to move radially inwardly. For example, the distal ends 316 of the mandrels can be coupled to the shoulder portions 305 to pull them inward as the mandrels move proximally. In other embodiments, the proximal portions 305 of the shoulder portions 304 can be resiliently biased toward the radially collapsed position, such that moving the distal ends 316 of the mandrels out from under them causes them to resiliently flex inwardly toward their natural collapsed position.

The shoulder portions 304 can comprise the same material as the main body 302, or different material can be used. For example the shoulder portions 304 can comprise a more flexible, elastic material and the main body 302 can comprise a more rigid material. Similarly, the mandrels 306 can comprise the same or different materials as the main body 302 and the shoulder portions 304. Exemplary materials include HDPE, HMWPE, HMWPU, and/or polypropylene. In some embodiments, the various portions of the dilator 300 can be coated with silicone and/or other materials to reduce friction and/or serve other purposes.

In some embodiments, the main body 302 and the shoulder portion 304 of the dilator 300 can be of one-piece unibody construction, such that the shoulder portions 304 are contiguous extensions from the main body rather that a separate piece that is attached to the main body. In such embodiment, the main body and the shoulder portions comprise the same materials.

In some embodiments, the dilator 300 can further comprise one or more spring mechanisms to deflect associated adjustable shoulder portions radially outwardly when the associated mandrels are not under the shoulder portion. The spring mechanism can comprise a pre-shaped nitinol flat wire positioned under the adjustable shoulder portion that is configured to deflect it outwardly. The wire can be resiliently deformed to a flat configuration when the shoulder portion is in the radially collapsed position.

FIGS. 15-20 show another exemplary vascular dilator 500 comprising a tapered distal portion 502, a proximal shaft portion 504, adjustable shoulder portions 506, and mandrels 508 for adjusting the shoulder portions 506. The dilator 500 is configured to be introduced through a vessel or chamber wall with an introducer sheath 520, as shown FIG. 19, positioned around the shaft portion 504 and abutting the shoulder portions 506. A guidewire lumen 516 extends through the length of the dilator. The dilator 500 can comprise two, three, four, or more shoulder portions 506, with a corresponding number of mandrels 508, though only two of each are illustrated.

In the illustrated embodiment, the two shoulder portions 506 are located on opposite sides of the distal end 502 of the dilator and extend around less than the entire circumference of the dilator. Each shoulder portion 506 can extend circumferentially less than 180°, less than 150°, less than 120°, and/or less than 90°, but have sufficient circumferential size to provide a smooth transition between the dilator and the sheath.

At the outer surfaces between the shoulder portions 506, the dilator 500 can have a smooth transition from the frustoconical distal portion 502 to the cylindrical shaft portion 504, such that no shoulder is present at these smooth transition regions between the shoulder portions 506.

Each shoulder portion 506 can include a flexible proximal portion 510 forming the outer surface, and a biasing mechanism that biases the flexible proximal portion 510 radially outwardly. The biasing mechanism can comprise a spring element 512, as illustrated, or other type of biasing mechanism. The spring element 512 can comprise a resilient material, such as Nitinol or other metals, and can be resiliently compressed under sufficient force to allow the proximal portion 510 of the shoulder to collapses inwardly.

Figure 17:
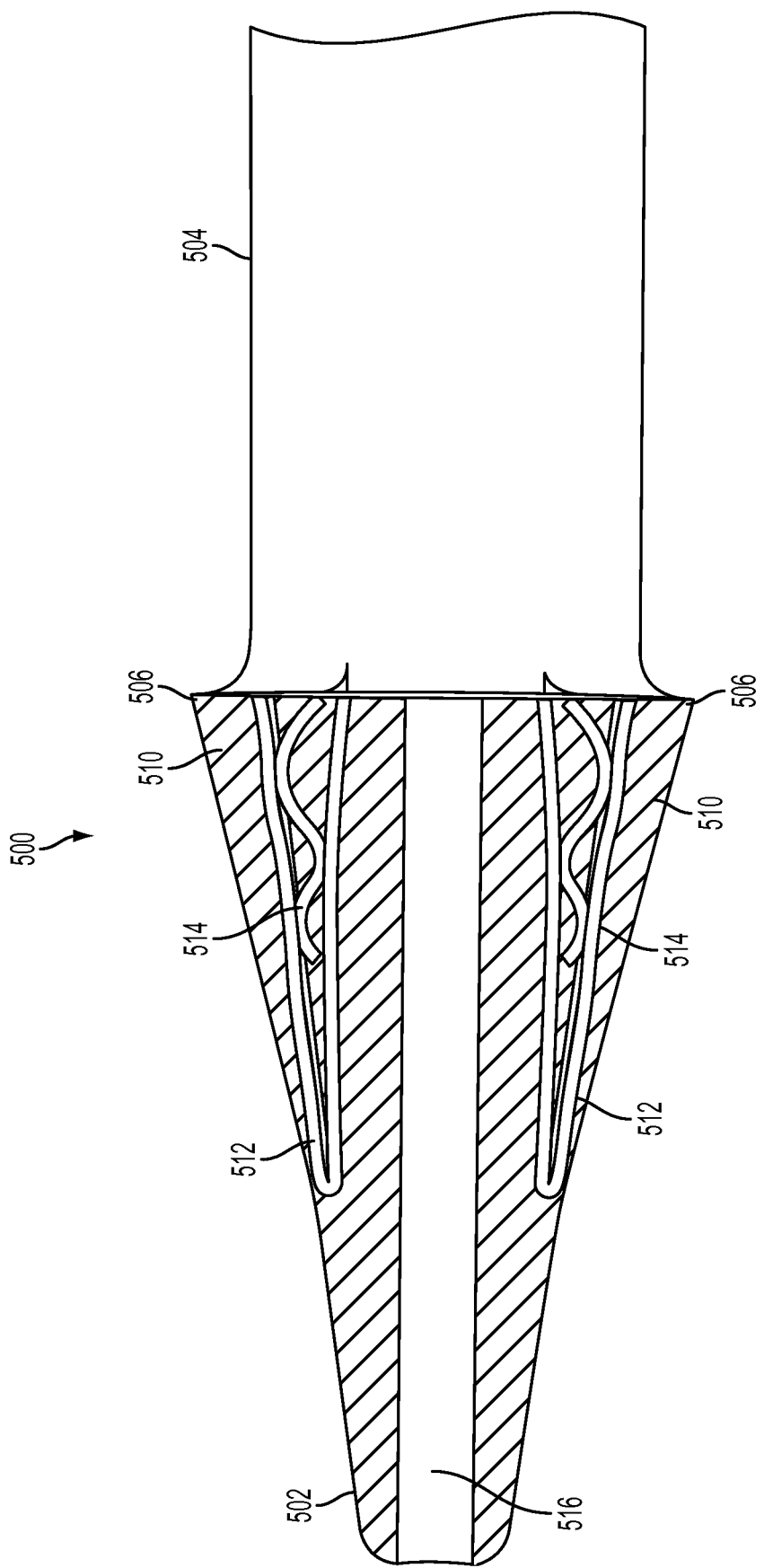
FIG. 17 is an enlarged side view of the dilator of FIG. 15, with the distal portion shown in cross-section.
Figure 18:
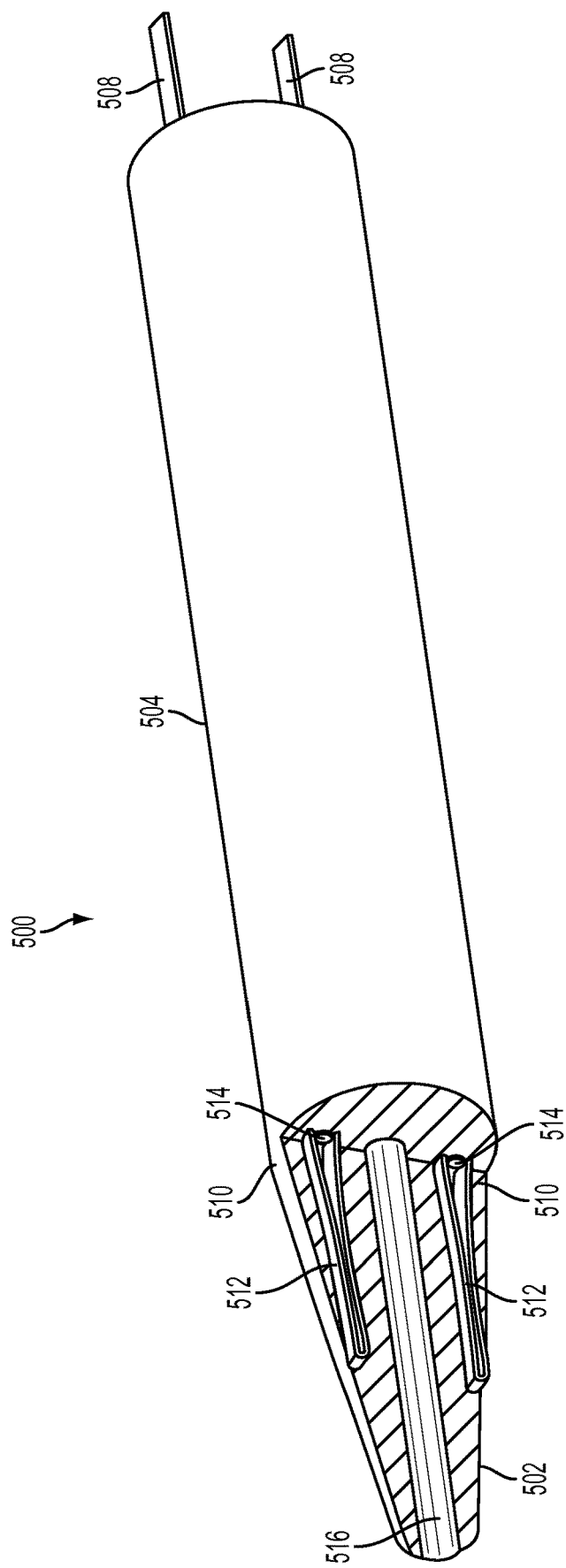
FIG. 18 is a perspective view of the dilator of FIG. 15, with the distal portion shown in cross-section, and with an adjustable shoulder portion shown in a radially collapsed configuration.

In some embodiments, the distal end 514 of each mandrel 508 can include a non-linear shape, such as a wavy shape as shown in FIG. 17, such that the distal end 514 can keep the spring element 512 spread apart when the mandrel 508 is slid distally. In this configuration, the presence of the distal end 514 between the arms of the spring element 512 prevents or restricts the ability of the spring element arms from resiliently collapsing, and thereby keeps the proximal shoulder portions 510 in the radially outward position, such as during insertion through a wall and during advancement of the dilator.

The mandrels 508 can slide longitudinally to cause the shoulder portions 506 to move between a radially collapsed position and a radially extended position. For example, an actuator at a proximal hub outside the vessel can control longitudinal motion of the mandrels 508 relative to the rest of the dilator 500. In the radially collapsed position (FIGS. 18 and 20), the mandrels 508 are slid proximally relative to the rest of the dilator 500, causing the distal ends 514 of the mandrels to move out from under a flexible proximal portion 510 of the shoulder and the spring element 512, allowing the proximal portions 510 of the shoulder portions and the outer arms of the spring elements 512 to articulate or bend radially inwardly. When the mandrels 508 are pulled proximally, the non-linear distal end 514 can resiliently flatten out as they are pulled into or through narrow passageways in the shaft portion 504 of the dilator. In the radially collapsed position, the maximum radial extent of the shoulder portions 506 can be about equal to, or less than, the radius of the shaft portion 504 of the dilator and/or less than the inner radius of the sheath 520.

In the radially extended position (FIGS. 15-17, and 19), the mandrels 508 are slid distally relative to the rest of the dilator 500, such that the distal ends 514 of the mandrels 508 move into the spring elements 512 and under the proximal portions 510 of the shoulder portions, causing the proximal portions 510 of the shoulder portions to move to, or remain at, a radial position extending beyond the radius of the shaft portion 504 and/or beyond the inner radius of the sheath 520, such that at least some of the distal end 522 of the sheath 520 is protected by the shoulder. During insertion into a vessel or chamber, the shoulder portions 506 can be positioned in the radially extended position, such that the shoulder portions 506 extend radially beyond the radius of the shaft portion 504, such as about even with the outer radius of the sheath 520 to provide a smooth transition and minimize tearing of the vessel wall during insertion.

To remove the dilator 500 from the vessel or chamber through an introducer sheath 520, the mandrels 508 can be moved proximally relative to the rest of the dilator 500 to allow the proximal portions 510 of the shoulder portions 506 to move radially inwardly to the radially collapse position. In some embodiments, the natural configuration of the shoulder portions 506 is the collapsed position, such that removal of the distal ends 514 of the mandrels from beneath the shoulder portions causes the shoulder portions to resiliently collapse inward. With the shoulder portions 506 in the collapsed position, the dilator 500 has little or no shoulder, presenting a smooth, transition between the tapered distal portion 502 and the shaft portion 504 all the way around the dilator. This allows the dilator 500 to be retracted through the sheath 520 with minimal contact between the shoulder and the distal end 522 of the sheath 520, which can reduce damage to the sheath.

In some embodiments, the distal end 522 of the sheath 520 contacts the shoulder portions 506 during retraction and forces them to collapse radially inwardly into the voids under the proximal portions 510 and between the arms of the spring element 514. In such embodiments, moving the mandrels 508 proximally out from under the shoulder portions 506 may not immediately cause the shoulder portions to collapse inwardly, and instead the shoulder portions remain extending radially outwardly, such as under the urging of the spring element 514, until the distal end 522 of the sheath 520 exerts a sufficient radially inward force on them, causing them to deflect inwardly, as shown in FIG. 20.

The shoulder portions 506 can comprise the same material as the rest of the distal portion 502 and the shaft portion 504, or different material can be used. For example the shoulder portions 506 can comprise a more flexible, elastic material and the rest of the distal portion 502 can comprise a more rigid material.

In some embodiments, the shoulder portions 506, the distal portion 502, and the shaft portion 504 of the dilator 500 can be of one-piece unibody construction, such that the shoulder portions 506 are contiguous extensions from the distal portion 502 rather that a separate piece that is attached.

Figure 14:
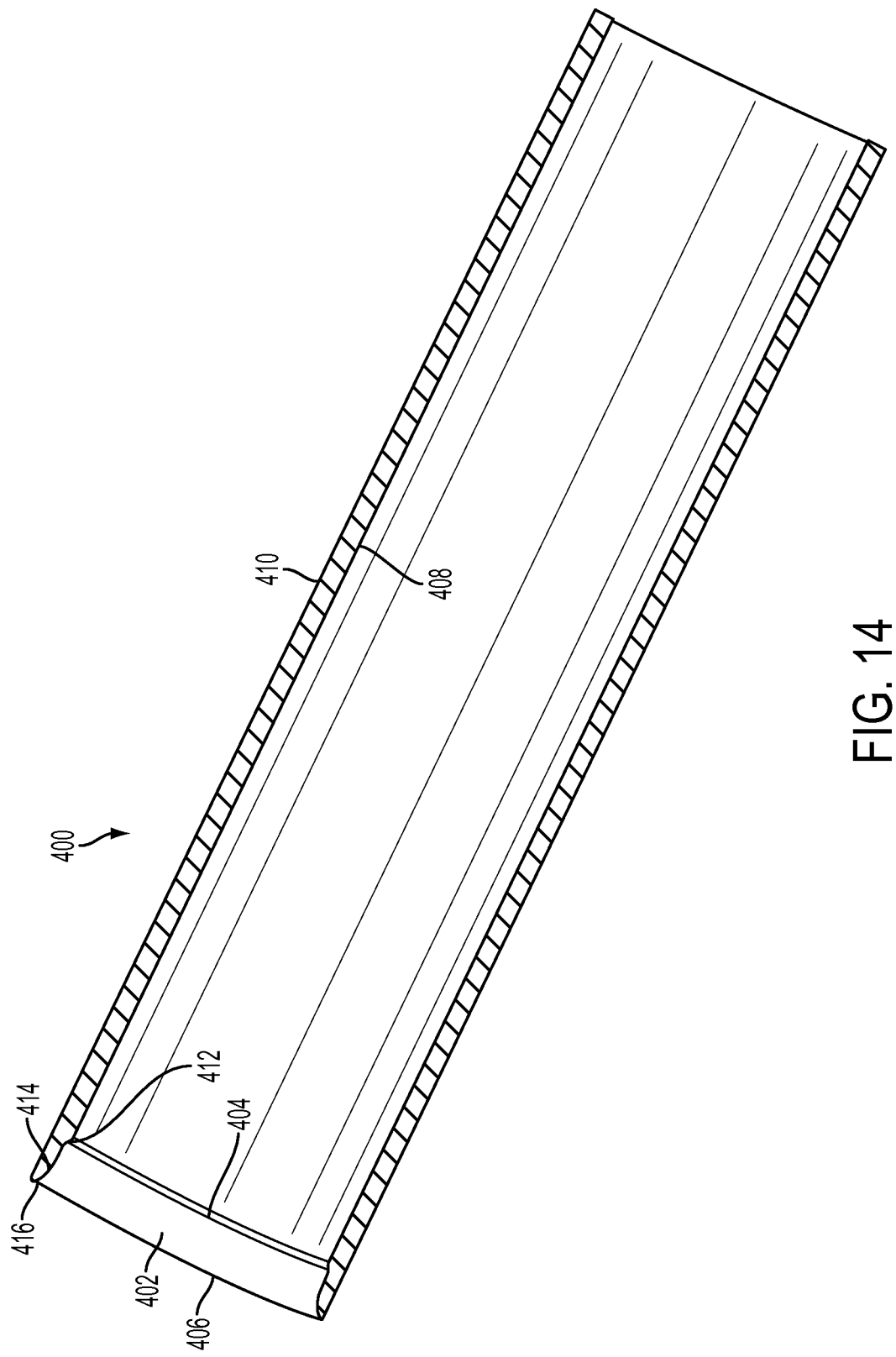
FIG. 14 is a perspective cross-sectional view of an exemplary introducer sheath, taken along its longitudinal axis.
Figure 15:
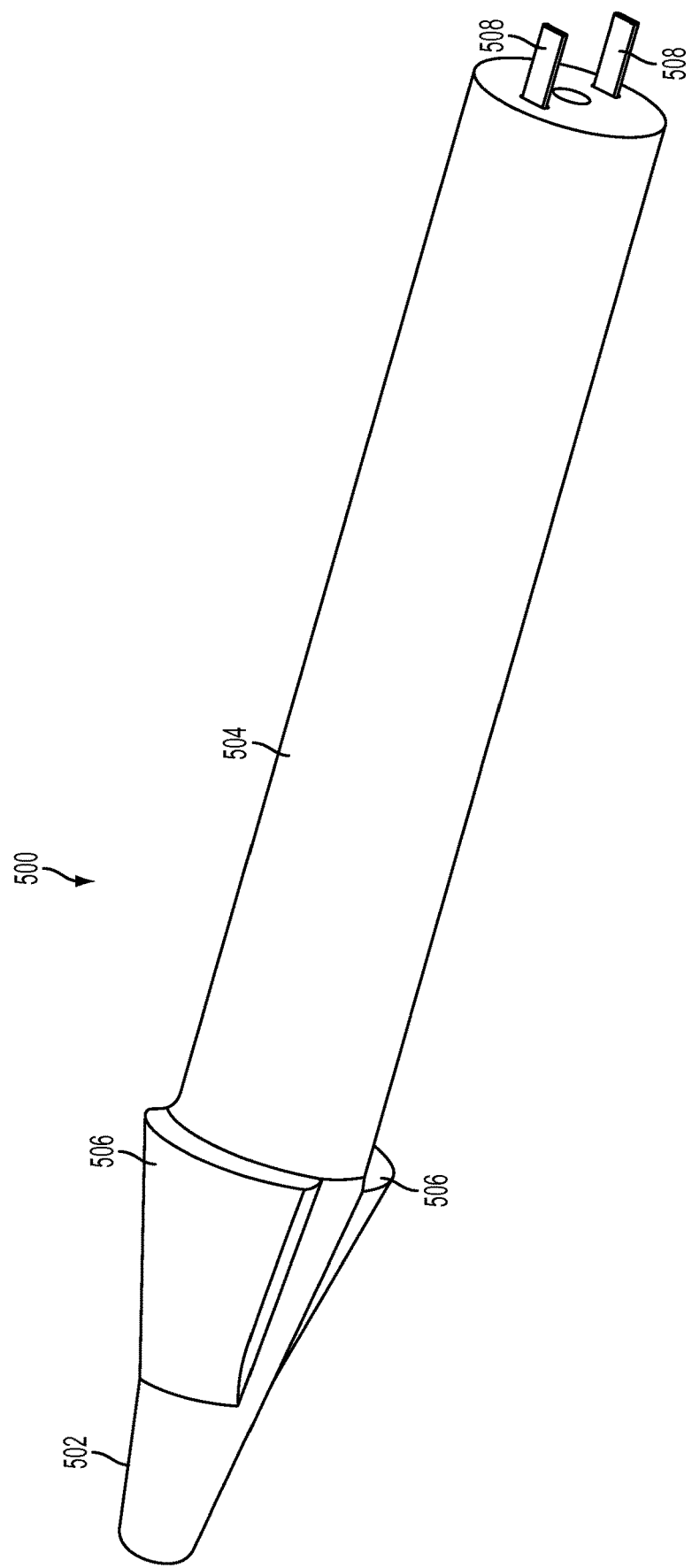
FIG. 15 is a perspective view of another exemplary vascular dilator.
Figure 16:
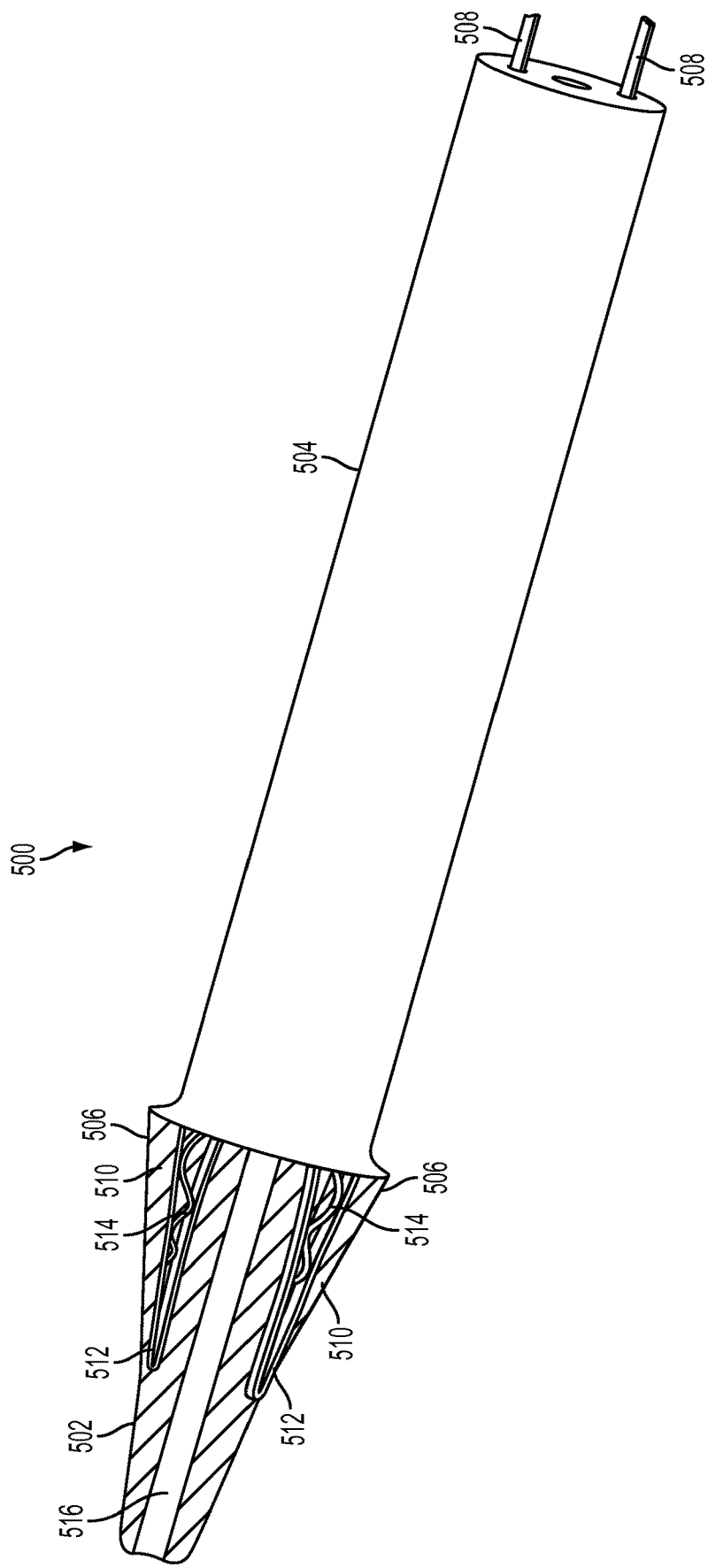
FIG. 16 is a perspective view of the dilator of FIG. 15, with the distal portion shown in cross-section.

FIG. 14 shows a cross-section of an exemplary introducer sheath 400, such as can be used with the dilators 100, 200, and 300 described above. Various other types of introducer sheaths can also be used with the dilators 100, 200, and 300. The sheath 400 includes an internally "beveled" distal portion 402 that gradually reduces in thickness moving from a transition point 404 toward the distal end 403 of the sheath. The transition portion 404 is the longitudinal position along the inner surface of the sheath 400 where the thickness of the sheath begins to reduce and/or the inner diameter begins to increase. Moving distally from the transition point 404, the inner surface 408 of the sheath slopes radially outwardly over a first inclined portion 412. From the distal end of the first inclined portion 412, a flat portion 414 begins. The inner surface 408 has a substantially constant inner diameter at the flat portion 414. Moving distally from the distal end of the flat portion 414, the inner surface 408 of the sheath slopes radially outwardly again over a second inclined portion 416 and terminates at the distal end 406, at which point the sheath 400 has a minimum thickness and the inner diameter approaches the outer diameter. The outer diameter of the sheath 400 can be substantially constant along the length of outer surface 410.

In other embodiments, the inner surface 408 of the sheath 400 can increases in inner diameter at a generally constant rate from the transition portion 404 to the distal end 406. The inner surface 408 can have other concave, convex, and/or partially linear slope profiles between the transition portion 404 and the distal end 406.

The gradual increasing of the inner diameter of the sheath 400 near the distal end 406 can help cause the shoulder of a segment of a dilator to deflect radially inward when is it retracted against the distal end of the sheath, enabling the dilator segment to slide through the inner lumen of the sheath. The inclined portions 412, 416 can act as a ramp to gradually cause the inward deflection of shoulder with proximal motion of the shoulder.

In addition, the reduced thickness of the sheath 400 at the distal end portion 402 can provide a degree of increases flexibility and deformability of the distal end portion 402 to further help the shoulder of a dilator enter into the sheath with minimal damage to the sheath.

In some embodiments, the "beveled" distal end portion of the sheath 400 can extend over only certain portions of the inner circumference of the sheath. For example, the "beveled" portions be located at discrete positions that match the circumferential positions of the shoulders of an associated dilator, such as the shoulder portions 304 of the dilator 300 or the shoulder portions 113 of the dilator 100. The sheath 400 can have a constant thickness and/or other types of tapering at other circumferential positions not aligned with the shoulders of an associated dilator.

The sheath 400 can comprise any suitable materials as is known in the art. In some embodiments, the distal end portion 402 of the sheath can comprise a different material than the rest of the sheath, such as a more pliant or more elastically deformable material that helps guide the shoulders of a dilator into the sheath and helps avoid damage to the distal end of the sheath.

The dilators and sheaths disclosed herein can be used in various medical procedures other than simple access into a blood vessel through a vessel wall. For example, the disclosed devices can be used for accessing one blood vessel from another blood vessel. In one such procedure, access to the descending aorta can be made from the inferior vena cava, by passing a disclosed device out through a wall of the inferior vena cave and in through a wall in the aorta, or vice versa, where the two vessels are adjacent to each other.

Figure 3:
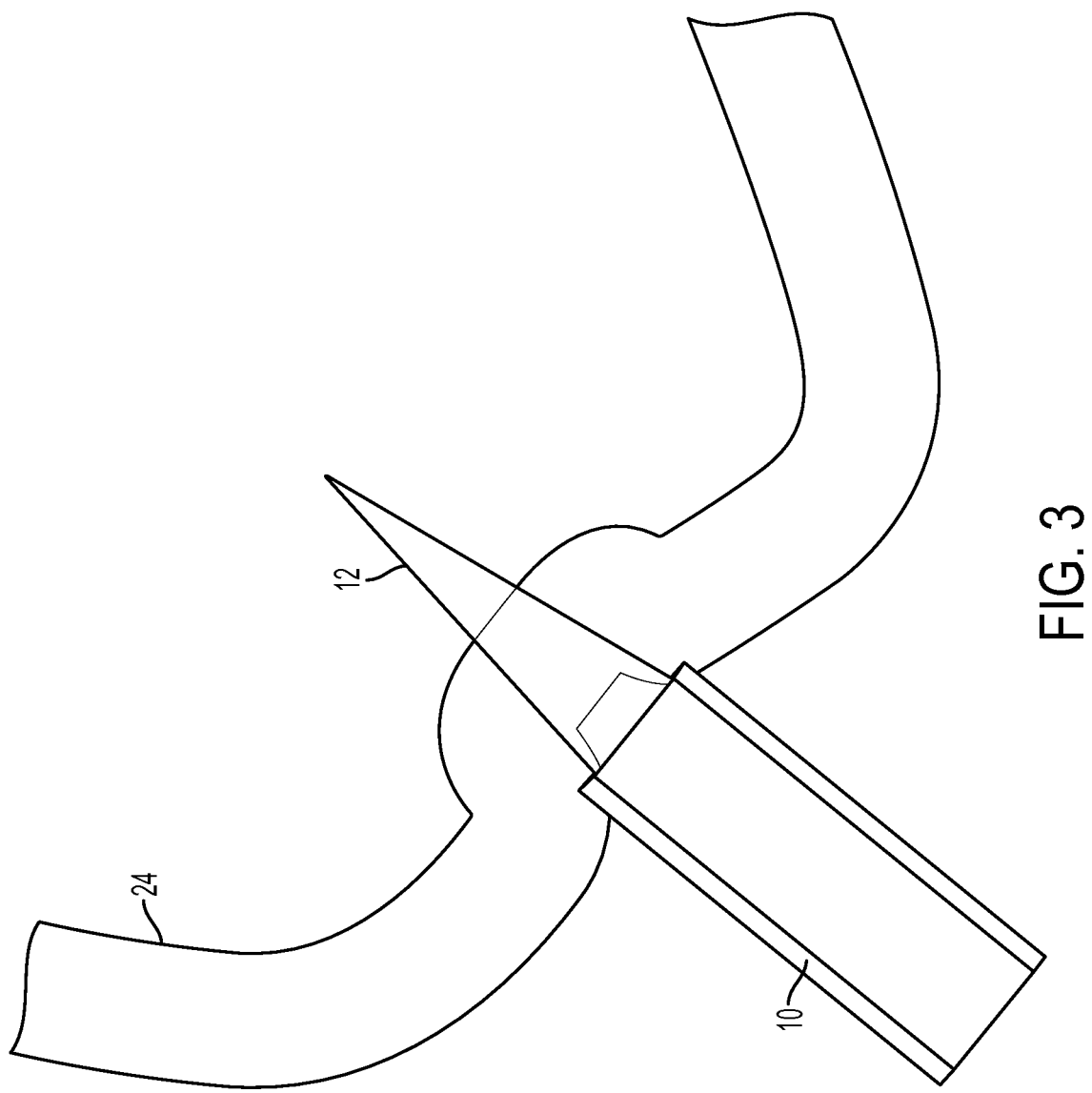
FIG. 3 shows a conventional dilator and introducer sheath entering the heart through the heart wall. The heart muscle is seen to "pucker" as it is displaced inward by the shoulder-free transition of the dilator (12) to the sheath (10). This may interfere with cardiac function during the procedure, risks excessive force during sheath advancement, and risks excessive injury to the heart.

For another example, the disclosed devices can be used during direct trans-thoracic assess through a heart wall into the heart. In such procedures, the disclosed devices can reduce dimpling or buckling of the heart wall at the transition between the dilator and the introducer sheath, as shown in FIG. 3, reducing unnecessary trauma to the heart wall. The issue of dimpling or buckling can also be reduced during access into blood vessels using the disclosed devices.

Explanation of Terms

Unless otherwise noted, technical terms are used according to conventional usage. In order to facilitate review of the various embodiments of the disclosure, the following explanation of terms is provided:

The terms "distal" and "distally" refer to a location or direction that is, or a portion of a device that when implanted (for example placed within a blood vessel) is, further downstream or farther away from the point of insertion. The terms "proximal" and "proximally" refer to a location or direction that is, or a portion of a device that when implanted, or placed within the blood vessel, is further upstream or closest to the point of insertion. The term "longitudinal" refers to the axis extending in the distal and proximal directions, or to the longitudinal axis of a cylindrical body or lumen.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. In addition, the materials, methods, and devices are illustrative only and not intended to be limiting.

In view of the many possible embodiments to which the principles of the disclosed technology may be applied, it should be recognized that the illustrated embodiments are only preferred examples and should not be taken as limiting the scope of the disclosure. Rather, the scope of the disclosure is defined as being at least as broad as the following exemplary claims. We therefore reserve the right to claim at least all that comes within the scope of these exemplary claims.

The invention claimed is:

1. A vascular dilator for use with an intravascular introducer sheath, the dilator comprising:
a first segment and a second segment that cooperatively form the dilator, the dilator comprising a nosecone tip, wherein the first and second segments are coupled together along a first interface that extends primarily in directions of a longitudinal axis of the dilator; and
wherein the first segment and the second segment are slidable longitudinally relative to one another along the interface for at least partial selective disassembly of the dilator to facilitate withdrawal of the dilator from the introducer sheath, the first segment being configured to deflect radially inwardly, which is perpendicular to the longitudinal axis toward the second segment, when the first segment is withdrawn through the introducer sheath.

2. The dilator of claim 1, wherein the second segment is retractable longitudinally through the introducer sheath during a first stage and then the first segment is retractable longitudinally through the introducer sheath during a subsequent stage.

3. The dilator of claim 1, wherein the dilator comprises a tapered distal portion and a generally cylindrical shaft portion proximal to the tapered distal portion, and wherein the tapered distal portion comprises a shoulder portion that extends at least partially around the tapered distal portion.

4. The dilator of claim 3, wherein the shoulder portion extends radially from a longitudinal centerline of the dilator farther than the shaft portion, the longitudinal centerline extending along the longitudinal axis of the dilator.

5. The dilator of claim 3, wherein the first segment comprises a first part of the shoulder portion and the second segment comprises a second part of the shoulder portion.

6. The dilator of claim 5, wherein the first part of the shoulder portion extends less than 180° circumferentially and the second part of the shoulder portion extends less than 180° circumferentially.

7. The dilator of claim 3, wherein the shoulder portion extends less than 360° circumferentially around the dilator.

8. The dilator of claim 3, wherein the shoulder portion in total extends 180° or less around the tapered distal portion.

9. The dilator of claim 3, wherein the shoulder portion extends radially beyond a radius of the shaft portion a distance about equal to a thickness of the intravascular introducer sheath.

10. The dilator of claim 1, wherein a shaft portion of the first segment is engaged with a shaft portion of the second segment such that the first segment is movable longitudinally relative to the second segment but non-longitudinal relative motion between the shaft portions of the first and second segments is restricted.

11. The dilator of claim 1, wherein the first segment comprises a recess located at least partially within a tapered distal portion of the first segment, and wherein a distal end portion of the second segment is configured to deflect inwardly into the recess of the first segment during retraction of the second segment.

12. The dilator of claim 1, further comprising a third segment coupled to the first and second segments along two interfaces that extend primarily longitudinally; and
wherein the third segment is slidable longitudinally relative to the first and second segments along the interfaces.

13. The dilator of claim 12, wherein the first, second, and third segments portions each comprise a portion of a shoulder that extends completely around the dilator.

14. The dilator of claim 1, wherein the first segment comprises a nosecone tip that defines a distal portion of a guidewire lumen passing through the dilator.

15. The dilator of claim 1, further comprising the introducer sheath sheath comprising a distal end portion that has a generally constant outer diameter and has an inner diameter that increases moving distally toward a distal end of the introducer sheath.

16. A method of using a vascular dilator with an introducer sheath, wherein the vascular dilator comprises first and second segments coupled together along a first interface that extends primarily in directions of a longitudinal axis of the dilator, the method comprising:
advancing the first segment of the dilator distally relative to the second segment of the dilator and the introducer sheath, the introducer sheath being positioned around proximal shaft portions of the first and second segments; and then
retracting the second segment proximally through the introducer sheath alongside the shaft portion of the first segment; and then
retracting the first segment proximally through the introducer sheath;
wherein retracting the second segment comprises causing a shoulder portion of the second segment to contact a distal end of the introducer sheath and thereby cause a distal portion of the second segment to deflect radially inwardly into a recess formed in the first segment, such that the shoulder portion of the second segment moves radially inwardly a sufficient distance to enter the introducer sheath.

17. The method of claim 16, wherein retracting the first segment comprises causing a shoulder portion of the first segment to contact the distal end of the introducer sheath and thereby cause a distal portion of the first segment to deflect radially inwardly a sufficient distance to enter the introducer sheath.

18. The method of claim 16, further comprising retracting a third segment of the dilator proximally through the introducer sheath prior to retracting the first segment, the third segment being engaged to the first and second segments along two interfaces that extend primarily in the directions of the longitudinal axis of the dilator.

19. The method of claim 16, wherein the method further comprises inserting the vascular dilator and the introducer sheath into a blood vessel through a vessel wall or into a heart through a heart wall, wherein the inserting is performed with the distal end of the introducer sheath positioned adjacent to a proximal surface of a shoulder of the dilator, the shoulder having a maximum radial dimension about equal to an outer radius of the introducer sheath.

20. The method of claim 16, wherein the method further comprises using the dilator and introducer sheath to access an aorta from an inferior vena cava.

21. The method of claim 16, wherein the method further comprises using the dilator and introducer sheath to access a heart chamber through a heart wall.

22. A method of using a vascular dilator with an introducer sheath, wherein the vascular dilator comprises first and second segments coupled together along a first interface that extends primarily in directions of a longitudinal axis of the dilator, the method comprising:
advancing the first segment of the dilator distally relative to the second segment of the dilator and the introducer sheath, the introducer sheath being positioned around proximal shaft portions of the first and second segments; and then
retracting the second segment proximally through the introducer sheath alongside the shaft portion of the first segment; and then
retracting the first segment proximally through the introducer sheath;
wherein retracting the first segment comprises causing a shoulder portion of the first segment to contact a distal end of the introducer sheath and thereby cause a distal portion of the first segment to deflect radially inwardly a sufficient distance to enter the introducer sheath.

23. The method of claim 22, further comprising retracting a third segment of the dilator proximally through the introducer sheath prior to retracting the first segment, the third segment being engaged to the first and second segments along two interfaces that extend primarily in the directions of the longitudinal axis of the dilator.

24. The method of claim 22, wherein the method further comprises inserting the vascular dilator and the introducer sheath into a blood vessel through a vessel wall or into a heart through a heart wall, wherein the inserting is performed with the distal end of the introducer sheath positioned adjacent to a proximal surface of a shoulder of the dilator, the shoulder having a maximum radial dimension about equal to an outer radius of the introducer sheath.

25. The method of claim 22, wherein the method further comprises using the dilator and introducer sheath to access an aorta from an inferior vena cava.

26. The method of claim 22, wherein the method further comprises using the dilator and introducer sheath to access a heart chamber through a heart wall.

* * * * *